United States Patent
Vogt et al.

(10) Patent No.: US 10,143,979 B2
(45) Date of Patent: Dec. 4, 2018

(54) DEVICE FOR MIXING AND STORING POLYMETHYL METHACRYLATE BONE CEMENT WITH PRESSURE PUMP AND AMPOULE BREAKER

(71) Applicant: Heraeus Medical GmbH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 34 days.

(21) Appl. No.: 15/479,919

(22) Filed: Apr. 5, 2017

(65) Prior Publication Data

US 2017/0291153 A1    Oct. 12, 2017

(30) Foreign Application Priority Data

Apr. 6, 2016 (DE) .................. 10 2016 106 261

(51) Int. Cl.
*B01F 7/00*      (2006.01)
*B01F 7/16*      (2006.01)
(Continued)

(52) U.S. Cl.
CPC .......... *B01F 7/161* (2013.01); *A61B 17/8833* (2013.01); *B01F 3/1221* (2013.01);
(Continued)

(58) Field of Classification Search
CPC .......... B01F 7/161; B01F 3/1221; B01F 7/20; B01F 11/0082; B01F 13/0033;
(Continued)

(56) References Cited

U.S. PATENT DOCUMENTS 4,671,263 A    6/1987 Draenert
4,758,096 A    7/1988 Gunnarsson
(Continued)

FOREIGN PATENT DOCUMENTS

DE    3 640 279 A1   6/1987
DE    69812726 T2    2/2004
(Continued)

OTHER PUBLICATIONS

Charnley, J.; "Anchorage of the Femoral Head Prosthesis of the Shaft of the Femur"; The Journal of Bone and Joint Surgery; Feb. 1960, pp. 28-30, vol. 42 B, No. 1, Manchester, England.
(Continued)

*Primary Examiner* — Anshu Bhatia
(74) *Attorney, Agent, or Firm* — Norris McLaughlin P.A.

(57) ABSTRACT

A device mixes bone cement and stores parent components of the bone cement. The device has a cartridge comprising an interior, that is closed on one side by a movable delivery plunger, a receptacle comprising side walls for receiving a monomer liquid container that are closed at least in some regions. The receptacle has at least one deformable closed side wall, a screen and/or a filter arranged below the receptacle so that the contents of the opened monomer liquid container flow through the screen and/or the filter. The device further has a connecting line through which the monomer liquid is to be routed into the interior of the cartridge, a hollow cylinder which is connected to the connecting line and which is connected to the receptacle by way of a fluid connection so that the hollow cylinder is arranged in a fluid line between the receptacle and the interior of the cartridge. A pump plunger is arranged in the hollow cylinder, which is axially displaceable in the hollow cylinder, and an opening device, which is movably mounted against the deformable side wall of the receptacle. The (Continued)

Figure 1:
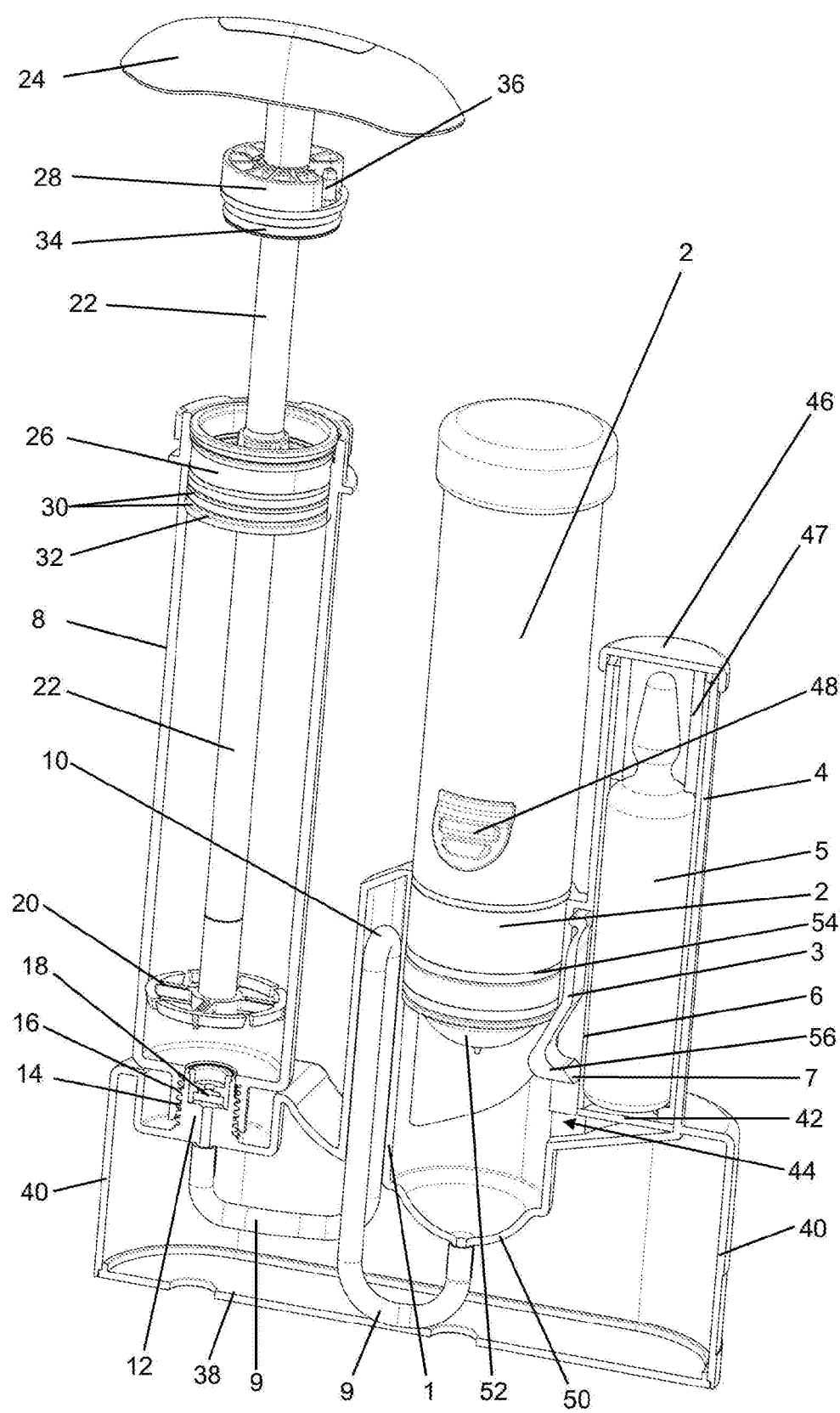

opening device extends into the hollow cylinder, wherein, by pressing the pump plunger into the hollow cylinder, the opening device is to be pressed against the deformable side wall of the receptacle so that the deformable side wall deforms such that a monomer liquid container located in the receptacle is to be opened by the pressure of the opening device.

25 Claims, 12 Drawing Sheets

(51) Int. Cl.
*A61B 17/88* (2006.01)
*B01F 3/12* (2006.01)
*B01F 7/20* (2006.01)
*B01F 15/00* (2006.01)
*B01F 15/02* (2006.01)
*B01F 11/00* (2006.01)
*B01F 13/00* (2006.01)

(52) U.S. Cl.
CPC ............ *B01F 7/20* (2013.01); *B01F 11/0082* (2013.01); *B01F 13/0033* (2013.01); *B01F 15/0087* (2013.01); *B01F 15/00974* (2013.01); *B01F 15/0206* (2013.01); *B01F 15/0237* (2013.01); *B01F 15/0258* (2013.01); *B01F 15/0278* (2013.01); *B01F 15/0279* (2013.01); *A61B 2017/8838* (2013.01); *B01F 2215/0029* (2013.01)

(58) Field of Classification Search
CPC ............ B01F 15/0087; B01F 15/00974; B01F 15/0206; B01F 15/0237; B01F 15/0258; B01F 15/0278; B01F 15/0279; B01F 2215/0029; A61B 17/8833; A61B 2017/8838
See application file for complete search history.

(56) References Cited

U.S. PATENT DOCUMENTS

| | | |
|---|---|---|
| 4,973,168 A | 11/1990 | Chan |
| 5,100,241 A | 3/1992 | Chan |
| 5,344,232 A | 9/1994 | Nelson et al. |
| 5,551,778 A | 9/1996 | Hauke et al. |
| 5,586,821 A | 12/1996 | Bonitati et al. |
| 5,588,745 A | 12/1996 | Tanaka et al. |
| 5,624,184 A | 4/1997 | Chan |
| 5,997,544 A | 12/1999 | Nies et al. |
| 6,033,105 A | 3/2000 | Barker et al. |
| 6,312,149 B1 | 11/2001 | Sjövall et al. |
| 6,709,149 B1 | 3/2004 | Tepic |
| 8,662,736 B2 | 3/2014 | Vogt et al. |
| 10,016,228 B2 * | 7/2018 | Vogt .................... B01F 11/0054 |
| 2010/0329074 A1 | 12/2010 | Vogt et al. |
| 2012/0325367 A1 | 12/2012 | Mathys et al. |
| 2015/0367301 A1 | 12/2015 | Vogt |
| 2016/0051304 A1 | 2/2016 | Vogt et al. |

FOREIGN PATENT DOCUMENTS

| | | |
|---|---|---|
| DE | 600 12 383 T2 | 9/2005 |
| DE | 10 2009 031 178 B3 | 9/2010 |
| DE | 10 2014 108 569 B3 | 10/2015 |
| EP | 0 692 229 A1 | 1/1996 |
| EP | 1 005 901 A2 | 6/2000 |
| EP | 1 016 452 A2 | 7/2000 |
| EP | 1 020 167 A2 | 7/2000 |
| EP | 1886647 A1 | 2/2008 |
| EP | 2 987 765 A1 | 2/2016 |
| WO | 94/26403 A1 | 11/1994 |
| WO | 99/67015 A1 | 12/1999 |
| WO | 00/35506 A1 | 6/2000 |
| WO | 2011/109915 A1 | 9/2011 |

OTHER PUBLICATIONS

Notice of Acceptance for corresponding to Australia Application No. 2017202223, issued by the Australian Patent Office dated Feb. 2, 2018.

* cited by examiner

DEVICE FOR MIXING AND STORING POLYMETHYL METHACRYLATE BONE CEMENT WITH PRESSURE PUMP AND AMPOULE BREAKER

This application claims foreign priority benefit under 35 U.S.C. 119 of German Application No. DE 10 2016 106 261.8 filed Apr. 6, 2016.

DESCRIPTION

The invention relates to a device for mixing polymethyl methacrylate bone cement and for storing the parent components of the bone cement. In particular, the invention relates to a device for mixing polymethyl methacrylate bone cement and for storing a monomer liquid and a cement powder as parent components of the bone cement.

The invention further relates to a method for mixing a bone cement, in particular a polymethyl methacrylate bone cement.

Polymethyl methacrylate (PMMA) bone cements can be traced back to the fundamental work of Sir Charnley (Charnley, J.: Anchorage of the femoral head prosthesis of the shaft of the femur. J. Bone Joint Surg. 42 (1960) 28-30.). PMMA bone cements consist of a liquid monomer component and a powder component. The monomer component generally contains the methyl methacrylate monomer and an activator (N,N-dimethyl-p-toluidine) dissolved therein. The powder component, also known as bone cement powder, comprises one or more polymers, an X-ray opaque and the initiator dibenzoyl peroxide. The polymers of the powder component are produced on the basis of methyl methacrylate and comonomers, such as styrene, methyl acrylate or similar monomers through polymerization, preferably suspension polymerization. When mixing the powder component with the monomer component, a plastically deformable paste, the actual bone cement, is obtained as a result of the polymers of the powder component swelling in the methyl methacrylate. When the powder component is mixed with the monomer component, the N,N-dimethyl-p-toluidine activator reacts with dibenzoyl peroxide, forming radicals. The radicals formed initiate the radical polymerization of the methyl methacrylate. As the polymerization of the methyl methacrylate continues, the viscosity of the cement paste increases until it solidifies.

The monomer most frequently used in polymethyl methacrylate bone cements is methyl methacrylate. Redox initiator systems usually consist of peroxides, accelerators and, if required, suitable reducing agents. Radicals are only formed when all elements of the redox initiator systems interact. For this reason, the elements of the redox initiator system are arranged in the separate parent components in such a way that these cannot trigger a radical polymerization. When the composition is suitable, the parent components are storage-stable. It is only when the two parent components are mixed to form a cement paste that the elements of the redox initiator system, which were previously stored separately in the two pastes, liquids or powders, react, forming radicals which trigger the radical polymerization of the at least one monomer. The radical polymerization then leads to the formation of polymers while using the monomer, wherein the cement paste hardens.

PMMA bone cements can be mixed in suitable mixing receptacles with the aid of spatulas by mixing the cement powder with the monomer liquid. The disadvantage of this procedure is that air inclusions can form, or can be present, in the cement paste created, which may negatively impact the mechanical properties of the hardened bone cement, and which can therefore later cause a destabilization of the bone cement.

In order to avoid air inclusions in the bone cement paste, a plurality of vacuum cementing systems have been proposed, of which the following are listed as examples: U.S. Pat. No. 6,033,105 A, U.S. Pat. No. 5,624,184 A, U.S. Pat. No. 4,671,263 A, U.S. Pat. No. 4,973,168 A, U.S. Pat. No. 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, and U.S. Pat. No. 5,344,232 A. With the vacuum cementing systems presented, it is necessary to connect an external vacuum pump in order to generate the reduced pressure. These are generally operated with compressed air using the Venturi principle. The compressed air required to operate the vacuum pumps is either taken from stationary compressed air facilities or from electrically actuated compressors. In addition, it is also possible to use electrically actuated vacuum pumps in order to generate the vacuum.

A further development in cementing technology includes cementing systems in which both the cement powder and the monomer liquid are already packaged in separate compartments of the mixing systems, and which are only mixed together in the cementing system directly before the cement application. Such closed full-prepacked mixing systems have been proposed in EP 0 692 229 A1, DE 10 2009 031 178 B3, U.S. Pat. No. 5,997,544 A, U.S. Pat. No. 6,709,149 B1, DE 698 12 726 T2 and U.S. Pat. No. 5,588,745 A. With these mixing systems, too, an external vacuum source is required.

The patent DE 10 2009 031 178 B3 discloses a generic mixing device with a two-piece delivery plunger for closing a cement cartridge. Here, a combination of a gas-permeable sterilization plunger and a gas-impermeable sealing plunger is used. This principle of a closed vacuum mixing system is realized with the closed PALACOS® PRO cementing system, which is produced and distributed by Heraeus Medical GmbH.

WO 00/35506 A1 proposes a device in which polymethyl methacrylate bone cement powder is stored in a cartridge, wherein the cement powder fills the entire volume of the cartridge and the intermediate spaces between the particles of the cement powder have such a volume that corresponds to the volume of the monomer liquid required for producing bone cement paste with the cement powder stored in the cartridge. This device is structured in such a manner that a vacuum causes the monomer liquid to be introduced into the cartridge from above, wherein, for this purpose, a vacuum is applied at a vacuum port on the underside of the cartridge. As a result, the monomer liquid is drawn through the cement powder, wherein the air located in the intermediate spaces of the cement particles is displaced by the monomer liquid. Here, no mechanical mixing with a stirrer of the cement paste formed is conducted.

The disadvantage of this system is that cement powders which swell quickly with the monomer liquid cannot be mixed with this device, since the quickly swelling cement powder particles form a gel-type barrier following penetration of the monomer liquid into the cement powder up to approximately 1 to 2 cm, and hinder the migration of the monomer liquid through the entire cement powder. Further, the possibility cannot be excluded with the vacuum influence that, following complete penetration of the cement powder by the monomer liquid, the monomer liquid is sucked off via the vacuum port. Then, insufficient monomer liquid is available for the hardening through radical polymerization, or the mixture ratio, and therefore also the consistency of the bone cement, is unintentionally altered. Further, it is problematic that the air trapped between the cement powder particles is to be displaced from above downwards by the monomer liquid, since the air, which is specifically lighter than the monomer liquid, has the desire, due to gravity, to wander upwards in the cement powder, rather than migrating downwards towards the vacuum port.

When vacuum mixing systems are used for cementing, external vacuum pumps must be provided. These vacuum pumps are high cost and must be cleaned following the application. Further, vacuum hoses are required to connect the vacuum pumps to the vacuum mixing systems. These vacuum hoses must be provided with the vacuum mixing systems. Before mixing with a vacuum mixing system, the vacuum pump must therefore first be assembled in the operating theatre (OP theatre) and connected to an energy source such as compressed air or electric power. The vacuum pump is then connected to the vacuum mixing system with a vacuum hose. These assembly steps cost valuable OP time and are open to possible error. The vacuum pump and the connecting lines to the vacuum mixing system and to external energy sources and supply lines require space and present potential stumbling hazards and obstacles that may interfere with the occasionally hectic procedure during an operation.

An interesting concept is proposed by EP 1 886 647 A1. Here, the cement powder is stored in an evacuated cartridge and the monomer liquid is located in a separate container. When the cartridge that is under pressure is opened, the monomer liquid is sucked into the cartridge without air flowing in. A bone cement paste is produced that is free of air inclusions. This concept requires that the cartridge remains closed in a vacuum-tight manner during storage prior to its use, and that no non-sterile air can penetrate. For this purpose, the cartridge must be stably hermetically sealed. The disadvantage of this is, therefore, that construction is complex and the content of the cartridge cannot be mixed, following sucking in of the monomer liquid, by a mixing system to be operated externally, since a feed-through for a mixing rod or a mixing tube cannot easily be rendered permanently vacuum-tight. All full-prepacked mixing systems known to date use vacuum or a reduced pressure to transfer the monomer liquid into the cement powder.

The object of the invention is therefore to overcome the disadvantages of the prior art. In particular, the disadvantages of the known vacuum mixing systems comprising an external vacuum source are to be overcome. Here, the invention has the object, among others, to develop a simple, closed device, in which polymethyl methacrylate bone cement powder (cement powder) and monomer liquid are stored in separate compartments and can then be mixed. The medical user should be able to combine and mix the polymethyl methacrylate bone cement powder with the monomer liquid within the device without the two cement components coming into contact with the medical user. Any contact of the medical user with the polymethyl methacrylate bone cement powder and with the monomer liquid should be excluded as far as possible. The device to be developed is a full-prepacked mixing system. The device should be designed in such a manner that a transfer of the monomer liquid into the polymethyl methacrylate bone cement powder can take place without the use of external vacuum pumps that are actuated by compressed air or compressors. It is further important that the device ensures in a functional and reliable manner the production of bone cement paste without external energy sources such as compressed air, vacuum or electric power, even under the simplest external conditions. The device should be usable autonomously without additional technical equipment. Further, in a second mode of operation, the device should permit a monomer transfer and a mixing of the cement components, including when an externally generated vacuum is used.

The device should be simplified to the extent that, with just one manual operating element, first the monomer liquid container or the glass ampoule can be opened, and only then, with the same operating element, without using an externally produced vacuum, a transfer of the monomer liquid into the cartridge with the cement powder contained in it can be conducted manually. This is designed to ensure that the medical user always first opens the monomer liquid container, and only then a manually generated monomer transfer or also, in the second mode of operation, a monomer transfer generated by an external vacuum, is possible. Faulty operation should be precluded as far as possible by the construction.

Further, the invention has the object of providing a device in which it is possible that the volume of monomer liquid that is transferred into the cement powder is systematically controlled, so that the ratio of the volume of monomer liquid to the cement powder quantity can be varied in order to control the consistency and therefore the processing properties of the bone cement.

A method should further be provided which enables a monomer transfer and a mixing in full-prepacked mixing systems, and in which only a single operating element must be operated in order to both open the monomer container and transfer the monomer liquid. Here, it should be possible to produce the mixing system to be developed mainly from low-cost plastic.

Further, a device that can be produced at low cost and which functions reliably for mixing a medical cement and, if necessary, for storing the parent components of the cement and a method for mixing the bone cement should be found in which the simplest possible manual operation for mixing the parent components can be applied, as far as possible without the necessity for using an external or additional energy source and without air inclusions arising in the mixed product.

The main component of the polymethyl methacrylate bone cement as a mixed product should be a powder, and the second component should be present in the form of a liquid. The two parent components of the bone cement should preferably be able to be stored separately in the full-prepacked mixing system, and to be securely combined while the device is in use.

The objects of the invention are achieved by a device for mixing polymethyl methacrylate bone cement and for storing the parent components of the bone cement, in particular a monomer liquid and a cement powder as parent components of the bone cement, the device having a cartridge comprising an interior for mixing the bone cement, wherein the interior is closed on one side by a movable delivery plunger, a receptacle comprising side walls for receiving a monomer liquid container, which side walls are closed at least in some regions, wherein the receptacle has at least one deformable closed side wall, a screen and/or a filter which is or are arranged below the receptacle so that the contents of the opened monomer liquid container flow through the screen and/or the filter, a connecting line through which the monomer liquid is to be routed into the interior of the cartridge, a hollow cylinder which is connected to the connecting line and which is connected to the receptacle by way of a fluid connection so that the hollow cylinder is arranged in a fluid line between the receptacle and the interior of the cartridge, wherein a pump plunger is arranged in the hollow cylinder, which is axially displaceable in the hollow cylinder, and an opening device, which is movably mounted against the deformable side wall of the receptacle, wherein the opening device extends into the hollow cylinder, wherein, by pressing the pump plunger into the hollow cylinder, the opening device is to be pressed against the deformable side wall of the receptacle so that the deformable side wall deforms in such a way that a monomer liquid container located in the receptacle is to be opened by the pressure of the opening device.

The fact that the hollow cylinder is arranged between the receptacle for the monomer liquid container, in particular for the glass ampoule (containing the monomer liquid), and the cartridge does not mean that the hollow cylinder must be geometrically arranged between them, but that the hollow cylinder is arranged between the receptacle and the cartridge in relation to the fluid line, i.e. the direction of flow of the monomer liquid, when this flows or is pumped out of the opened monomer liquid container in the direction of the cartridge.

In order for the monomer liquid to flow out of the opened monomer liquid container (in particular the glass ampoule) into the hollow cylinder, the receptacle is, for this purpose, connected to the hollow cylinder by the fluid connection, preferably via a mouth.

In order for the monomer liquid to be able to flow without the influence of additional force, the device must be correctly installed so that gravity produces the desired direction of flow. Accordingly, the terms "top" and "bottom" used within the context of the present invention, as well as "above" and "below", and "highest" and "lowest", are always in relation to the correct installation of the device.

The interior of the cartridge preferably has a cylindrical geometry. The cylindrical shape is the simplest with which the interior of the cartridge and the hollow cylinder can be realized. A cylindrical shape is, in geometric terms, the shape of a general cylinder with any base area, i.e. not only a cylinder with a circular base. The inner wall of the interior can therefore be a cylinder with any base, and the casing of the hollow cylinder can be a cylinder with any base, i.e. also with a non-circular or non-round base. According to the invention, however, a cylindrical geometry with a rotationally symmetrical, and in particular a circular, base is preferred since these are easiest to produce.

It can be provided according to the invention that a supporting element is provided opposite the deformable side wall. This ensures that the mechanical force which can be applied with the opening device onto the deformable side wall can influence the monomer liquid container, preferably the glass ampoule, in such a manner that this is broken open or pierced open, or torn open, or opened, and does not evade or is not pushed away.

Particularly preferably, the fluid connection opens into the hollow cylinder in the casing of the hollow cylinder.

According to the invention, a glass ampoule is preferably used as a monomer liquid container. Glass ampoules are particularly suitable as monomer liquid containers, since the monomer liquid can be stored for a particularly long period of time in them.

A monomer liquid container with several chambers for storing the monomer liquid can also be used. A monomer liquid container is therefore also understood within the context of the present invention as being a plurality of separate, individual partial monomer liquid containers, which can be installed in the receptacle and which can be opened with the opening device by deforming the deformable side wall of the receptacle.

In devices according to the invention, it can be provided that the monomer liquid is able to flow out of the opened monomer liquid container into the hollow cylinder, and the connecting line connects the hollow cylinder to the interior of the cartridge in such a way that, by means of the pump plunger, monomer liquid is to be pressed out of the hollow cylinder through the connecting line into the interior of the cartridge as a result of pressing the pump plunger into the hollow cylinder.

As a result, it is achieved that, after the monomer liquid container is opened, the pump plunger can at the same time be used to transfer the monomer liquid into the interior of the cartridge, and, respectively, as an actuator for pressing the monomer liquid into the interior of the cartridge. Here, the pump plunger can be actuated manually or by means of an internal energy store, in particular a tensioned pressure spring.

In order to achieve a good pump action and to avoid monomer liquid exiting the pump plunger, the pump plunger closes in a fluid-tight manner with the inner walls of the hollow cylinder. For this purpose, at least one circumferential seal can be provided, which closes the pump plunger with the inner walls of the hollow cylinder. The pump plunger is cylindrically shaped in some regions, at least in the area of the intended stroke, and forms a negative of the hollow cylinder.

The polymethyl methacrylate bone cement is preferably mixed from at least two components, or can be produced from at least two components. It is particularly preferred that one component is liquid (the monomer liquid), and the other is a powder (the cement powder).

According to the invention, the parent components for the mixed product, in particular for the PMMA bone cement, are already contained in the cartridge and in the monomer liquid container, preferably in a glass ampoule as a monomer liquid container, wherein the monomer liquid container is particularly preferably arranged in the receptacle. According to the invention, the device is preferably also suitable for storing the parent components, in particular when the monomer liquid container containing the monomer liquid is already inserted into the device.

It can further be provided according to the invention that a mixing device, which is externally operable, is arranged in the cartridge, wherein the mixing device is preferably operable by way of a mixing rod which is guided through a feed-through in the delivery plunger into the interior of the cartridge and which is movably mounted.

Particularly preferably, the mixing rod in the feed-through is supported in such a manner that it is rotatable and displaceable in the longitudinal direction. By means of the mixing device, the content of the interior of the cartridge can be conveniently mixed with the mixing rod. When low-viscous bone cements are used, the use of a mixing rod and a mixing device is not necessary, since the monomer liquid has displaced the air of the pore chambers between the cement powder particles before the cement powder swells, and has moistened the cement powder particles.

Within the context of the present invention, it can be provided that the delivery plunger is impermeable for powder, wherein preferably a pore filter is arranged in the delivery plunger, which is permeable for gas and impermeable for powder.

The pore filter can preferably be designed as a pore disc. Due to the impermeability for powder, the cement powder can be prevented from being able to escape from the interior of the cartridge. If the delivery plunger is gas-permeable, the interior can be evacuated by the delivery plunger and sterilized with a gas such as ethylene oxide.

According to a preferred further development of the present invention, it can be provided that the cement powder is contained in the interior of the cartridge.

It can also be provided that the monomer liquid is contained in the monomer liquid container in the receptacle. As a result, the device creates a finished full-prepacked mixing system which does not need to be filled with the cement powder prior to use. In the cartridge, the cement powder is stored separately from the monomer liquid in the monomer liquid container before use.

It can further be provided that a filter which is impermeable to the cement powder and permeable to the monomer liquid is arranged between the connecting line and the interior of the cartridge.

As a result, the cement powder can be prevented from penetrating into the connecting line, and polymerizing there during introduction of the monomer liquid, thus blocking or clogging the connecting line.

According to a further development, it can also be provided that the device has a stand in which at least part of the connecting line is arranged, wherein the cartridge is releasably connected to the stand, in particular releasably connected to the stand by way of a screw thread, wherein the filter which is impermeable to the cement powder and permeable to the monomer liquid is preferably optionally arranged in the stand of the device, particularly preferably arranged in the connection between the cartridge and the stand.

As a result, the device can be easily installed and is easy to operate.

Here, it can be provided that the hollow cylinder and the receptacle are connected to the stand, preferably connected non-detachably and/or in one piece to the stand. As a result, a particularly simple and low-cost structure of the device is enabled.

It can further be provided that the receptacle leads into the hollow cylinder at a circumferential surface of the hollow cylinder.

As a result, it can be ensured that all of the monomer liquid can flow into the hollow cylinder and can fill the hollow cylinder. Additionally, in this manner, air can exit the hollow cylinder at this point in a particularly easy manner.

It can be provided that a screen or filter is arranged in or on the fluid connection to the hollow cylinder, with which fragments of the opened monomer liquid container can be retained.

A further development of the invention relating to the use of gravity as an actuator for the flow of monomer liquid into the hollow cylinder proposes that the receptacle for the monomer liquid container is arranged above the fluid connection to the hollow cylinder.

As a result, the monomer liquid can flow through the fluid connection into the hollow cylinder due to gravity after the monomer liquid container has been opened.

Preferred devices according to the invention can also be characterized in that the connecting line is connected to the hollow cylinder at the bottom side, preferably at the lowest point of the hollow cylinder, wherein the pump plunger is particularly preferably arranged on the opposite side of the hollow cylinder.

As a result, all of the monomer liquid can flow out of the hollow cylinder, or be pressed out by the pump plunger.

It can further be provided that the hollow cylinder has, on the side opposite the pump plunger, a conical, semi-conical or otherwise downwardly tapering base, wherein the face of the pump plunger which faces the base of the hollow cylinder preferably forms a negative shape of the base.

As a result, all of the monomer liquid can flow out of or be pressed out of the hollow cylinder by the pump plunger. This means that the entire monomer liquid flows to the lowest point of the hollow cylinder, and no dead areas are present in which monomer liquid remains when the pump plunger is actuated. Due to the adaptation of the shape of the pump plunger to the inner shape of the hollow cylinder, the entire monomer liquid is pressed out of the hollow cylinder by the pump plunger when the pump plunger is moved in the direction of the opening to the connecting line, without residues of the monomer liquid remaining in the hollow cylinder. Further, this conical or spherical or matching design of the front side of the pump plunger ensures that, when the pump plunger is moved downwards or in the direction of the stand, the air above the monomer liquid in the hollow cylinder can escape through the fluid connection in the casing surface of the hollow cylinder, and no air bubbles remain above the monomer liquid while the monomer liquid is being transferred into the interior of the cartridge or into the cement powder.

Preferred embodiments may provide that the pump plunger can be axially moved in the hollow cylinder manually, preferably be pressed axially into the hollow cylinder manually.

This makes it possible to manually press the monomer liquid out of the hollow cylinder and transfer it into the interior of the cartridge.

In order to simplify operation and to provide greater variability of devices according to the invention, it can also be provided that the hollow cylinder is transparent and comprises markings regarding the filling level of a liquid in the hollow cylinder.

As a result, a quantity of the monomer liquid determined by the markings can be filled into the hollow cylinder, or pressed out of the hollow cylinder into the interior of the cartridge. As a result, it is possible to use the device to produce a bone cement paste with a consistency specified by the quantity of monomer liquid. Alternatively, the hollow cylinder can also not be transparent, and markings can be provided on the end of the pump plunger that protrudes out of the hollow cylinder in order to enable a defined propulsion of the pump plunger and therefore be able to press a defined volume of monomer liquid out of the hollow cylinder. With such structures, it is therefore possible to press both the entire volume of the monomer liquid out of the hollow cylinder into the cement powder in the interior of the cartridge, and to transfer only certain partial volumes of the monomer liquid out of the hollow cylinder into the cement powder. As a result, the ratio of monomer liquid to powder quantity can be adjusted, enabling the time at which the cement paste is no longer sticky and the viscosity of the bone cement to be controlled in a targeted manner.

A further development of the present invention proposes that the device has a tensioned pressure spring and at least one detent, wherein the pressure spring and/or the pump plunger is or are releasably arrested by the detent, wherein the pressure spring exerts a pressure on the pump plunger when the detent is released so that the pump plunger is pressed into the hollow cylinder.

These measures have the advantage that the operation of the device is facilitated. In addition, possible erroneous operation procedures can be prevented in this way. The arresting can be realized by buckles or securing pins as latching means or latching devices.

It can further be provided that the delivery plunger is connected by a releasable latching device to the cartridge, wherein the latching device can be released manually, in particular by the effect of axial force, so that the delivery plunger can be moved axially in the interior of the cartridge.

As a result, an undesirable movement of the delivery plunger can be avoided, such as can be caused, for example, by a vacuum in the interior of the cartridge.

As an alternative, it can also be provided that the hollow cylinder comprises an inner thread and the pump plunger comprises an outer thread matching thereto, so that the pump plunger is screwable into the hollow cylinder in order to press the opening device against the deformable side wall and to press the monomer liquid out of the hollow cylinder into the interior of the cartridge.

Likewise, as a result of this, a defined quantity of the monomer liquid can be pressed out of the hollow cylinder into the interior of the cartridge. This provides the possibility of using the device to produce a bone cement paste with a consistency which is determined by the quantity of the monomer liquid.

To avoid that the interior of the cartridge is inadvertently filled with monomer liquid, it can be provided that the connecting line between the hollow cylinder and the interior of the cartridge has an upwardly pointing loop, wherein the highest point of the loop is located above the mouth of the receptacle leading into the hollow cylinder.

It can therefore be prevented that the monomer liquid, during filling into the hollow cylinder, already passes through the connecting line into the interior of the cartridge. This inverted U-shaped loop of the connecting line achieves the situation that, before the movement of the pump plunger in the direction of the connecting line to the cartridge, the monomer liquid in the hollow cylinder remains in the connecting line up to the height of the vertex, as a result of which a premature admission of the monomer liquid to the cement powder is prevented. With high-viscosity cements in particular, a premature contact of even small quantities of the monomer liquid with the cement powder can lead to the clogging of the connecting line or of a line means configured as a nozzle, as described in U.S. Pat. No. 8,662,736 B2. The connecting line can be transparent or translucent, in order for the user to be able to monitor the monomer transfer visually. For this purpose, in particular, a viewing window can be provided in the device, through which the loop with the highest vertex can be identified.

It can further be provided according to the invention that the volume in the hollow cylinder is smaller than or equal to the volume of the monomer liquid in the monomer liquid container.

This prevents that, at the actuation of the pump plunger, air can be pressed into the cement powder.

It can further be provided that the interior of the cartridge is connected on the underside to the connecting line such as to allow the passage of liquid.

The connecting line can open, on the face side of the interior, into a nozzle in accordance with U.S. Pat. No. 8,662,736 B4. This nozzle prevents the ingress of cement powder into the line means.

In another embodiment variant, the interior of the cartridge is connected on a side casing surface to the connecting line such as to allow the passage of liquid. It is therefore also possible for the monomer liquid to be transferred laterally into the cement powder, into the interior of the cartridge.

Preferably, the hollow cylinder, the cartridge and the connecting line, as well as, if present, the stand, the mixing device and the mixing rod, are made of a plastic, and can be economically produced by plastic injection molding.

Preferably, it can also be provided that the opening device is a lever which is mounted against the receptacle to be rotatable about an axis, wherein a free end of the lever is pressable against the deformable side wall of the receptacle by the pump plunger, so that the free end of the lever deforms the deformable side wall in such a way that a monomer liquid container located in the receptacle and matching the receptacle is to be opened by the pressure of the free end of the lever, in particular is to be broken open or split open or punctured.

As a result, a particularly simple and economically realizable opening device is provided, which is not prone to defects and which can be easily activated by the movement of the pump plunger.

Here it can be provided that the free end, with the lever, is arranged inside the hollow cylinder, and abuts against the deformable side wall, in such a way that the lever, starting from the axis with the free end and the deformable side wall, forms a triangle with a web as a leg opposite the corner formed by the axis of rotation, wherein the triangle is arranged in the hollow cylinder.

This allows for the triangle to be pivoted about the axis of rotation due to axial movement of the pump plunger, as a result of which the deformable side wall is deformed with the free end in order to open the monomer liquid container in the receptacle.

Here it can be provided that the ratio of the length of the lever, starting from the point of rotation of the axis as far as the contact with the web, to the length of the web from the contact point of the web on the lever to the tip of the free end, is at least 3 to 1, preferably 4 to 1, and particularly preferably greater than 5 to 1.

Preferably, it can be provided here that the lever is arranged at a longitudinal side of a window-type opening above the fluid connection, rotatable by means of a hinge, in such a way that the axis of rotation of the lever stands perpendicular to the longitudinal axis of the hollow cylinder, wherein the hinge is arranged outside the hollow cylinder, on its outer casing surface.

It can further be provided that the free end of the lever is formed as a wedge, which abuts against the deformable side wall of the receptacle. Particularly preferably, the lever comprises a web, which is aligned perpendicular to the axis of rotation of the hinge, wherein, particularly preferably, the free end of the lever delimits the one end of the web.

A further development of the present invention proposes that the receptacle is a hollow cylinder and/or the receptacle consists of an elastomer or comprises an insert made of an elastomer, wherein the elastomer preferably has a Shore hardness of greater than 60, wherein the elastomer is particularly preferably a silicone rubber or an ethylene propylene diene rubber (EPDM).

Due to the cylindrical geometry of the receptacle, it is achieved that a cylindrical glass ampoule, as a monomer liquid container, can be inserted with a firm mounting into the receptacle. With the Shore hardness value indicated, it is achieved that the glass ampoule can be safely opened inside the receptacle without the receptacle being destroyed or a leak developing.

It can further be provided that a shoulder for supporting the monomer liquid container is arranged in the receptacle, wherein the shoulder is smaller than half the area of the base of the monomer liquid container or the cross-section of the monomer liquid container.

As a result, the monomer liquid container, in particular the glass ampoule, is fixed in the receptacle, so that it can be opened or broken open in a defined position with the aid of the opening device, and cannot deviate from this. The shoulder is preferably arranged in the receptacle in such a way that the distance between the shoulder and the liquid-permeable screen and/or filter is equal to or greater than the diameter of the monomer liquid container or of the glass ampoule.

It can also be provided that, upon a movement of the pump plunger into the hollow cylinder, a free end of the opening device presses on the deformable side wall in such a way that the vector of the force has a component which is directed towards the screen and/or filter and/or which presses a monomer liquid container inserted in the receptacle into the receptacle, preferably in the direction of the shoulder.

As a result, it is achieved that the monomer liquid container cannot be pressed out of the receptacle at the movement of the opening device, and the positioning of the monomer liquid container is secured. This leads to the situation that the monomer liquid container is safely opened, and cannot deviate out of the receptacle due to a movement.

It can be provided that a wedge is arranged at the free end of the opening device, in particular at the free end of the lever, on the side facing the receptacle.

By means of the wedge, a defined force is exerted onto a small surface area of the monomer liquid container, such that the monomer liquid container can be broken open with the least possible expenditure of force at a most precisely possible defined point. This wedge can be triangular or wedge-shaped. It is also possible for the wedge to be configured in the form of a pyramid, prism or cone.

It can further be provided that a monomer liquid container, in particular a glass ampoule, is arranged in the receptacle, which contains a liquid, preferably a monomer liquid, for producing a medical bone cement.

As a result, the device can be used directly to open the monomer liquid container or the glass ampoule without the monomer liquid container or the glass ampoule having to be inserted beforehand.

It can further be provided according to the invention that the opening device extends into the hollow cylinder above the fluid connection.

This ensures that first the monomer liquid container is opened, runs out, and the monomer liquid is able to flow out of the monomer liquid container through the fluid connection into the hollow cylinder, before the monomer liquid is pressed by the pump plunger out of the hollow cylinder through the connecting line into the cartridge.

The present invention also proposes that the pump plunger is fixable in place by a manually releasable latching device which, after an axial displacement of the pump plunger over the opening device in the hollow cylinder, locks the pump plunger above the mouth of the fluid connection to the receptacle in the hollow cylinder, so that the pump plunger in the hollow cylinder is not movable over the mouth of the fluid connection when the latching device is not released, wherein the latching device is preferably arranged on or in the pump plunger or extends through the pump plunger.

As a result, it is achieved that the pump plunger first operates the opening device, as a result of which the monomer liquid container in the receptacle is opened, and is then held by the latching device. Accordingly, until the latching device is released to allow for a further movement of the pump plunger into the hollow cylinder, sufficient time remains in order for the monomer liquid to be able to run out of the monomer liquid container into the hollow cylinder. This ensures that an adequate quantity of the monomer liquid is available in the hollow cylinder before it is pressed by the pump plunger into the cartridge.

The objects which underlie the present invention are also achieved by a method for mixing a bone cement, in particular with a device according to the invention, having the chronological steps:

A) a pump plunger is pressed into a hollow cylinder, wherein an opening device is pressed against a deformable side wall of a receptacle as a result of the movement of the pump plunger, B) a monomer liquid container containing a monomer liquid is opened as a result of the deformation of the side wall of the receptacle by the opening device, C) the monomer liquid flows out of the opened monomer liquid container and into the hollow cylinder, D) the pump plunger is pressed further into the hollow cylinder and the monomer liquid is thereby pressed out of the hollow cylinder and through a connecting line into the interior of a cartridge, wherein a cement powder is located in the interior of the cartridge, E) the monomer liquid and the cement powder are mixed in the interior of the cartridge.

Preferably, the monomer liquid flows into the hollow cylinder under the effect of gravity.

Likewise preferably, the monomer liquid flows through a screen and/or a filter into the hollow cylinder. The screen and/or the filter can retain fragments of the monomer liquid container which may be incurred by breaking open the monomer liquid container.

In methods according to the invention it can be provided that the movement of the pump plunger is stopped by a latching device in step A) and the latching device is released prior to step D) to enable the pump plunger to be pressed further into the hollow cylinder.

This avoids that, shortly after the opening of the monomer liquid container, the pump plunger is already pressed so far into the hollow cylinder that the monomer liquid cannot flow further into the hollow cylinder, and, as a result, is not be available in an adequate quantity in the hollow cylinder.

It can further be provided that the pump plunger is pressed into the hollow cylinder by a tensioned spring element, wherein preferably, for this purpose, a latching means or a detent, which engages in the pump plunger and/or in the spring element, is released beforehand.

As a result, the force which is required to press the pump plunger into the hollow cylinder does not have to be applied manually. The method is thereby further automated.

Moreover, it can be provided that the pump plunger, before step D), is secured by a latching device or a detent against the hollow cylinder, wherein the latching device or detent is released before the pump plunger, in step D), is pressed further into the hollow cylinder.

As a result, an undesirable movement of the pump plunger into the hollow cylinder is avoided.

It can be provided according to the invention that the monomer liquid and the cement powder are not mixed in the interior of the cartridge until the pump plunger has been pressed into the hollow cylinder fully or as far as a marking, wherein the marking is a measure for the monomer liquid introduced into the interior of the cartridge.

As a result, it can be ensured that the bone cement paste produced has the desired consistency, due to the desired admixture of monomer liquid.

A further development of the method according to the invention proposes that the monomer liquid and the cement powder are mixed in the interior by a mixing device in that the mixing device is operated by moving a mixing rod, which is guided into the interior of the cartridge to be rotatable and longitudinally displaceable, wherein, after the mixing process, the mixing rod is preferably withdrawn from the interior of the cartridge until it comes to a stop and, after being withdrawn until it comes to a stop, the mixing rod is particularly preferably broken off at a predetermined breaking point.

As a result, the method can be easily carried out by manual operation.

It can also be provided that the cartridge containing the fully mixed cement paste is released from the connecting line, the hollow cylinder and the receptacle, and the fully mixed cement paste is delivered from the interior of the cartridge by the propulsion of a delivery plunger, which is mounted to be axially movable in the cartridge and which delimits the interior of the cartridge on one side.

As a result, the cement paste can be used without major effort, and can be applied later to a patient.

Finally, it can also be provided that the monomer liquid is additionally sucked into the cartridge by a vacuum in the interior of the cartridge, wherein the vacuum in the cartridge is preferably effected by evacuating the interior of the cartridge by means of the delivery plunger arrested against the cartridge.

As a result, the transfer of the monomer liquid into the cartridge can be supported. Additionally, the quantity of air inclusions or the risk of the occurrence of air inclusions can be further reduced. The vacuum can theoretically be produced by the movement of the pump plunger, in that the pump plunger creates a reduced pressure on its rear side, which is transferred via the arrested delivery plunger into the interior of the cartridge.

The invention is based on the surprising recognition that, due to the movement of a pump plunger, an opening device can be operated with which a glass ampoule containing a monomer liquid can be opened. It has surprisingly been found, moreover, that the monomer liquid can then, with the aid of the same movement of the same pump plunger, be pressed from below into the interior of a cartridge, without any undesirable air inclusions being formed in the bone cement. As a result, with the use of the device it is possible to widely do without external energy sources or internal energy stores. A tensioned spring can trigger or, respectively, support the movement of the pump plunger. In particular, there is no need to make use of vacuum sources and vacuum-tight connections and components, which substantially facilitates use in less developed locations and use locally or in field hospitals. In addition, full-prepacked mixing systems according to the invention are less prone to possible defects, and are therefore ready for use with a very high degree of probability, since no vacuum leaks can occur.

The invention is further based on the surprising recognition that it is possible with the device according to the invention for a glass ampoule to be broken open over a large surface area inside the device or the cementing device respectively, so that the monomer liquid flows out of the glass ampoule in a short time and is ready for mixing with a medical bone cement powder. With the aid of a simple lever as the opening device, it is possible for the pressure onto the glass ampoule to be directed towards the seat of the glass ampoule in the receptacle, so that any deviation of the glass ampoule out of the receptacle can be excluded. At the same time, a very precisely defined local pressure can be exerted onto the glass ampoule, with which the glass ampoule can be broken open in the device. With the aid of the deformable side wall it can be ensured that the force is transferred through this side wall into the interior of the receptacle onto the glass ampoule, wherein the receptacle remains closed during the process. Any emergence of the monomer liquid from the receptacle can therefore be excluded. With the aid of the screen and/or filter, any glass splinters which may be incurred at the opening of the glass ampoule can be kept back. The monomer liquid can then be used for mixing with the bone cement powder.

For example, with a device according to the invention or a method according to the invention, it can be provided that, after the opening of the glass ampoule due to the movement of the opening device, which is induced by the movement of the pump plunger, the monomer liquid flows under gravitational force into a hollow cylinder, from which, by manual actuation of the pump plunger, it is pressed into the interior of a cartridge, which contains the cement powder. This means that, by contrast with the previous commercially conventional mixing systems, the transfer of the monomer liquid takes place not by way of vacuum but by pressure effect, and that the same pressure, in passing or as a side effect, is used to actuate the opening device, and is therefore used to break open the glass ampoule, which contains the monomer liquid. Such a manually actuated monomer transfer by pressure effect can be realized economically with simple plastic components which can be produced by plastic injection molding. The particular advantage of the device according to the invention lies in the fact that the device can be operated without external aids, such as vacuum pumps actuated by compressed air, and without external energy sources, such as compressed air or electricity. The device according to the invention can therefore be used autonomously, and can even be used under very primitive operating conditions. With the device according to the invention, a closed full-prepacked mixing system is provided for price-sensitive markets.

It has been found within the framework of the present invention that, with the introduction caused by pressure of the monomer liquid into the cement powder from the underside of the interior of the cartridge, the monomer liquid moves in the form of a unified front from the bottom upwards to the top. As a result, the air which is present in the intermediate spaces between the cement powder particles is displaced and pressed out upward. Air inclusions are therefore avoided. Surprisingly, it has been found within the framework of the present invention that a bone cement paste produced with a device according to the invention and a method according to the invention is very largely free of air inclusions, and in quality corresponds to a cement paste mixed under vacuum.

A device according to the invention for the storage and mixing of polymethyl methacrylate bone cement can for example comprise:

a) a first hollow cylinder as a cartridge interior, wherein a first face side of the first hollow cylinder is closed with at least one delivery plunger which is impermeable to cement powder, and wherein the second face side of the first hollow cylinder is impermeable to cement powder, as a result of which a first cavity is formed by the delivery plunger and the first hollow cylinder delimited by the second face side, in which cement powder is arranged, b) wherein the first cavity is connected via a first opening, impermeable to cement powder but permeable to liquid, with a liquid-permeable line means, to a cylindrical second cavity in a second hollow cylinder, c) wherein arranged on the casing surface of the second hollow cylinder is a second opening, permeable to liquids, which connects the second cavity in a liquid permeable manner to a hollow body, arranged outside the second hollow cylinder, which contains at least one monomer liquid container, wherein the hollow body is arranged above the opening in the casing surface of the second hollow cylinder, d) wherein arranged on the casing surface of the second hollow cylinders is a window-type third opening, above the second opening, wherein a lever is arranged on a longitudinal side of the window-type third opening, rotatable on a hinge, in such a way that the rotation axis of the lever stands perpendicular to the longitudinal axis of the second hollow cylinder, e) wherein the hinge is arranged outside the second cavity, on the outer casing surface of the second hollow cylinder, f) wherein arranged at the lever end, opposite the rotation point of the hinge, is a wedge, the wedge shape of which points outwards, opposed to the longitudinal axis of the second hollow cylinder, g) wherein the wedge is aligned in the direction of a deformable wall, which forms at least a part of a third hollow body which accommodates the at least one monomer liquid container, h) wherein the wedge element with the lever, with the monomer liquid container unopened, is arranged in the interior of the second hollow cylinder in such a way that the lever, projecting from the hinge, forms a triangle with the wedge and the deformable wall, which is arranged at least in some regions in the second cavity, i) wherein at least a part of the monomer liquid container is arranged behind the deformable wall opposite the wedge of the lever, j) a pump plunger arranged in the cylindrical second cavity, which is arranged above the window-type third opening of the second hollow cylinder, and k) wherein the pump plunger can be displaced axially in the second hollow cylinder in such a way that the lever with the wedge can be pressed against the deformable wall by the axial movement of the pump plunger.

An exemplary method which can, for example, be implemented with such an exemplary device, can be realized in that a) by an axial displacement of the pump plunger in the second cavity, downwards in the direction of the foot part, the lever is pivoted outwards in the direction of the deformable wall of the window-type third opening, wherein the lever is rotated about the hinge, b) the lever presses the deformable wall of the second cavity outwards, and thereby opens the at least one monomer liquid container, c) the monomer liquid flows under gravitational force through the second opening in the casing surface of the second hollow cylinder into the second cavity, d) after the transfer of the monomer liquid out of the at least one monomer liquid container into the second cavity, the pump plunger is pressed manually in the direction of the foot part of the device, e) as a result, the monomer liquid is pressed through the line means into the first cavity into the cement powder, f) after the transfer of the monomer liquid from the second cavity into the first cavity, the mixture of cement powder and monomer liquid is mixed manually by actuation of a mixing rod, g) then the mixing rod is drawn upwards and the mixing rod is broken off at a predetermined breaking point, and h) then the first hollow cylinder is separated from the food part.

As an alternative, the following method according to the invention can be implemented with the exemplary device:

a) by an axial displacement of the pump plunger in the second cavity downwards in the direction of the foot part, the lever is pivoted outwards in the direction of the deformable wall (the deformable side wall) of the window-type third opening, wherein the lever is rotated about the hinge, b) the lever presses the deformable wall of the second cavity outwards, and thereby opens the at least one monomer liquid container, c) the monomer liquid flows under gravitational force through the second opening in the casing surface of the second hollow cylinder into the second cavity, d) after the transfer of the monomer liquid out of the at least one monomer liquid container into the second cavity, an externally produced vacuum is applied to the delivery plunger of the first hollow cylinder, as a result of which the monomer liquid is sucked through the line means into the first cavity into the cement powder, e) after the transfer of the monomer liquid from the second cavity into the first cavity, the mixture of cement powder and monomer liquid is mixed manually by the actuation of a mixing rod, and the mixing rod is then drawn upwards and broken off at a predetermined breaking point, and f) the first hollow cylinder is separated from the foot part.

A further exemplary method which can be carried out with the device is characterized by the following sequential steps:

a) by an axial displacement of the pump plunger in the second cavity downwards in the direction of the foot part, the lever is pivoted outwards in the direction of the deformable wall of the window-type third opening, wherein the lever is pivoted about the hinge, b) the lever presses the deformable wall of the second cavity outwards, and thereby opens the at least one monomer liquid container, c) the monomer liquid flows under gravitational force through the second opening in the casing surface of the second hollow cylinder into the second cavity, d) after the complete transfer of the monomer liquid into the second cavity, a latching device of the pump plunger is released, wherein a pressure spring presses the pump plunger in the direction of the foot part of the device, e) as a result, the monomer liquid is pressed through the line means into the first cavity into the cement powder, f) wherein, after the transfer of the monomer liquid from the second cavity into the first cavity, the mixture of cement powder and monomer liquid is mixed manually by the actuation of a mixing rod, wherein the mixing rod is then drawn upwards and broken off at a predetermined breaking point, and g) the first hollow cylinder is then separated from the foot part.

Figure 2:
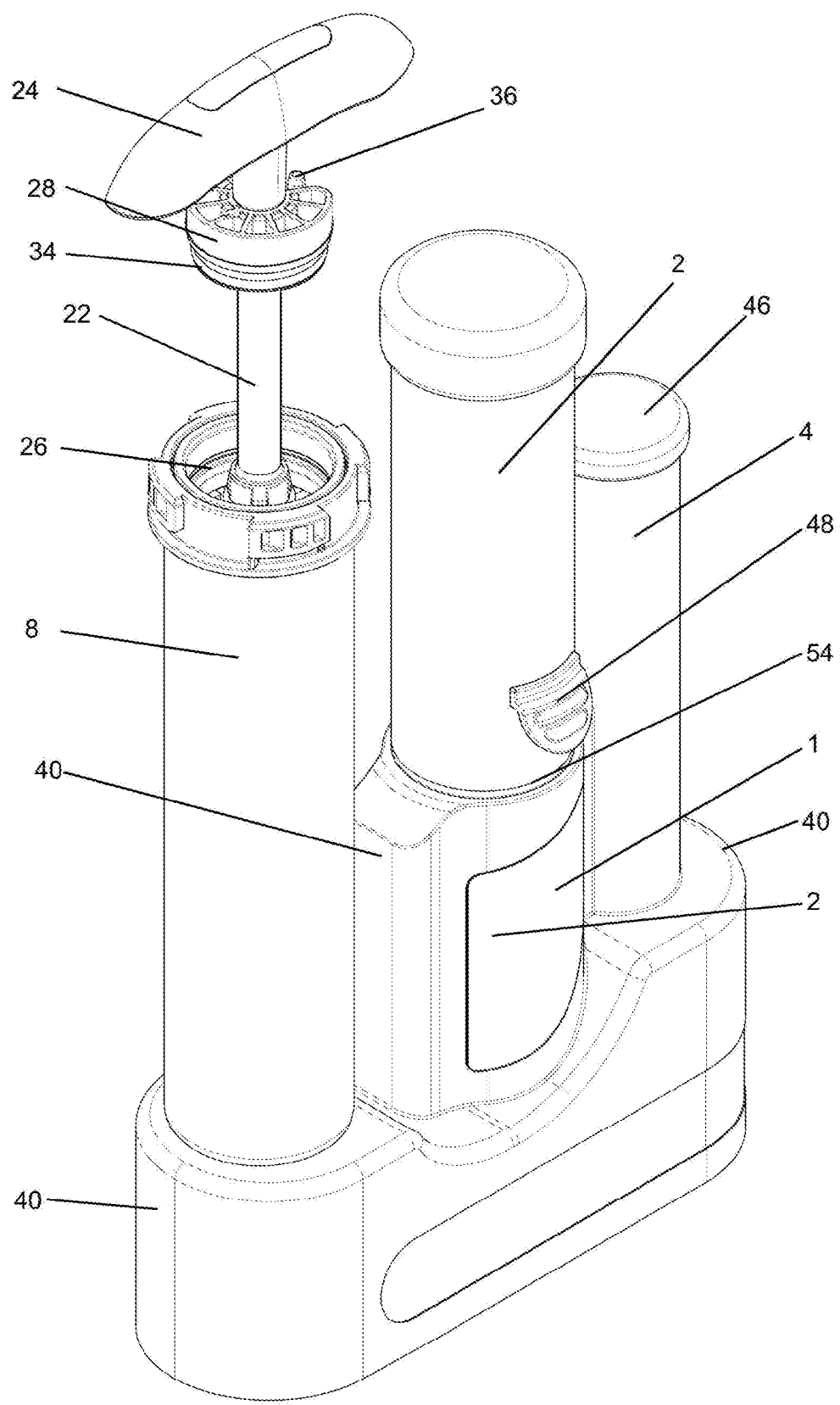
Figure 3:
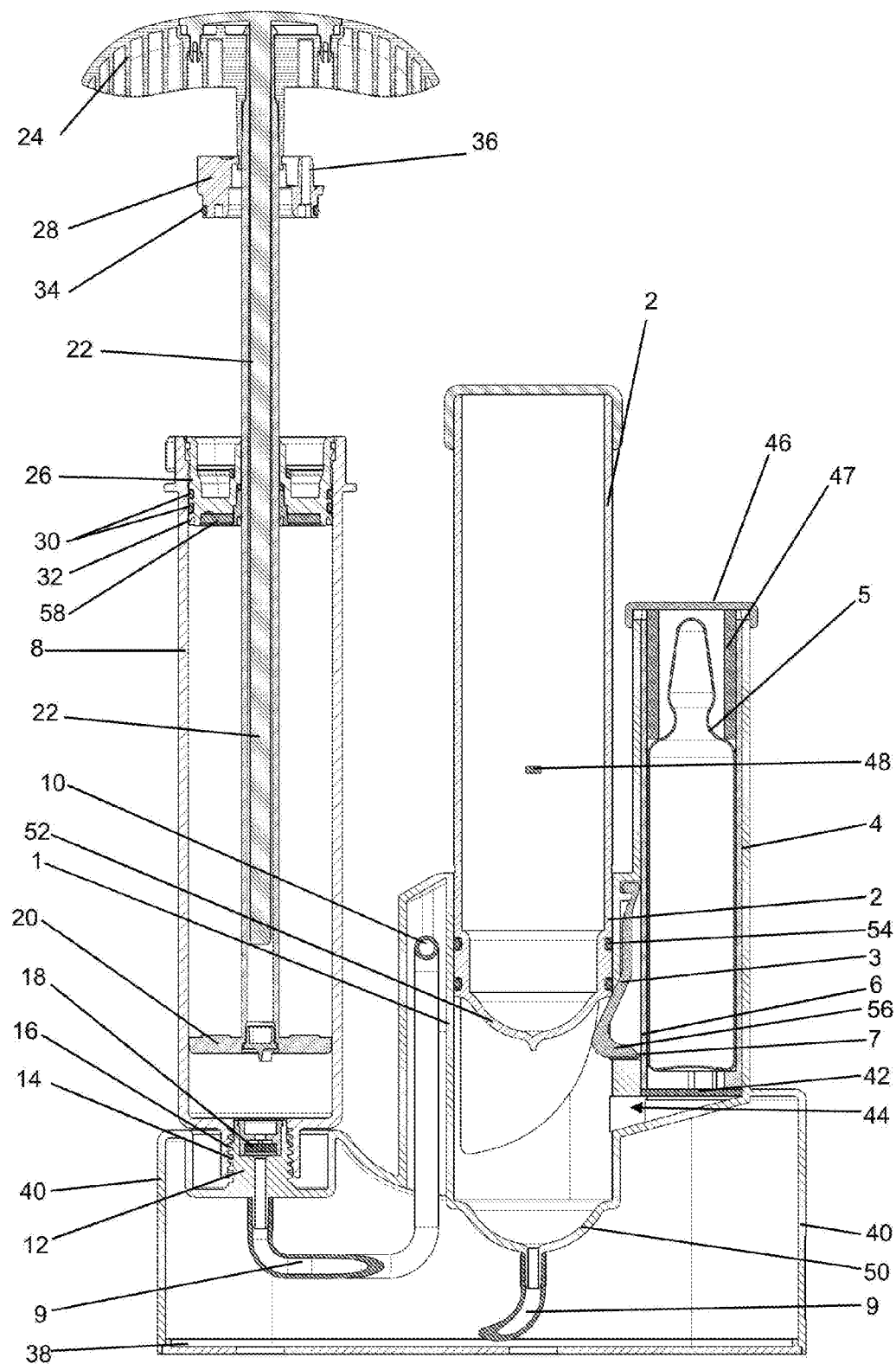
Figure 4:
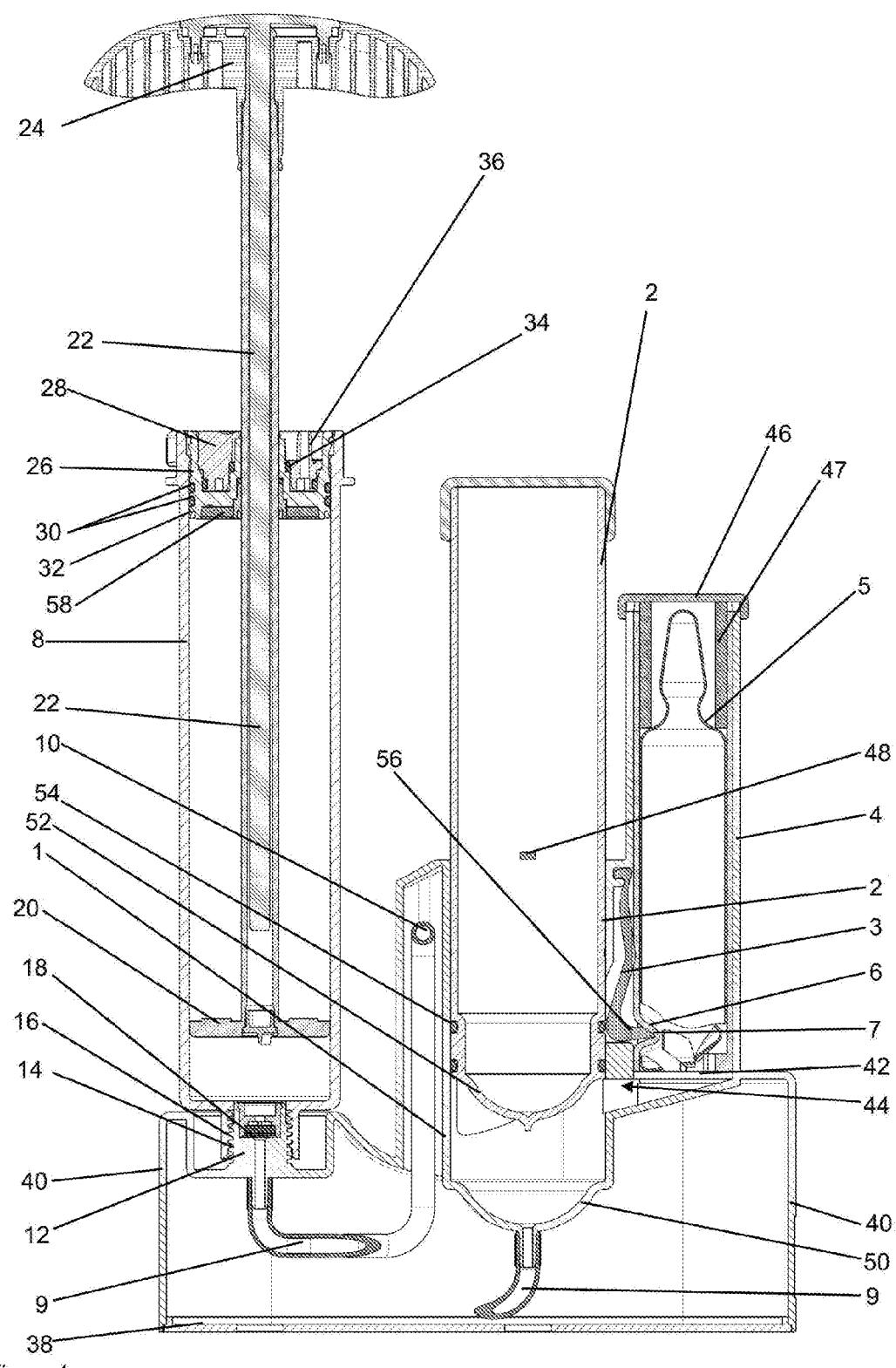
Figure 5:
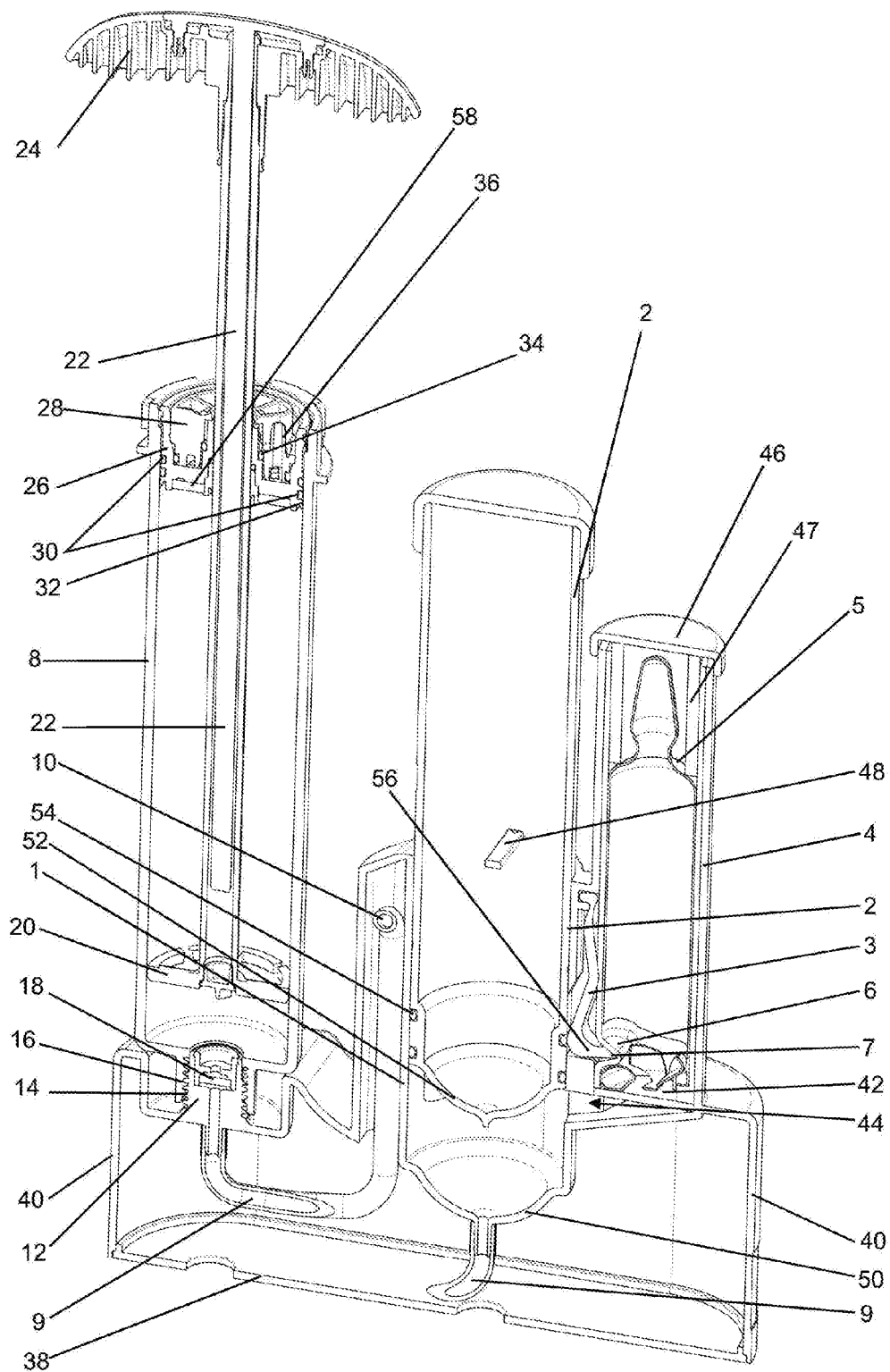
Figure 6:
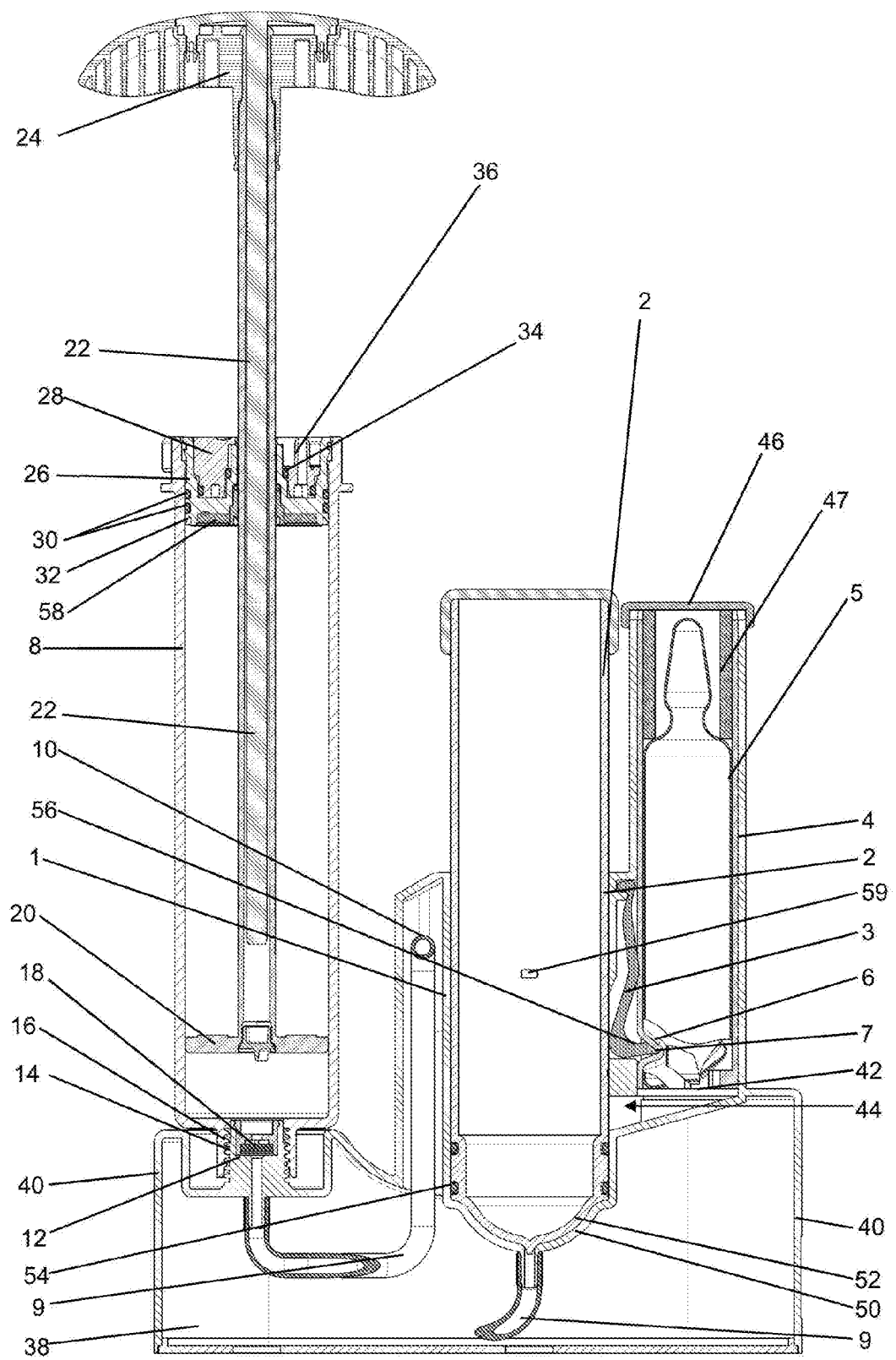
Figure 7:
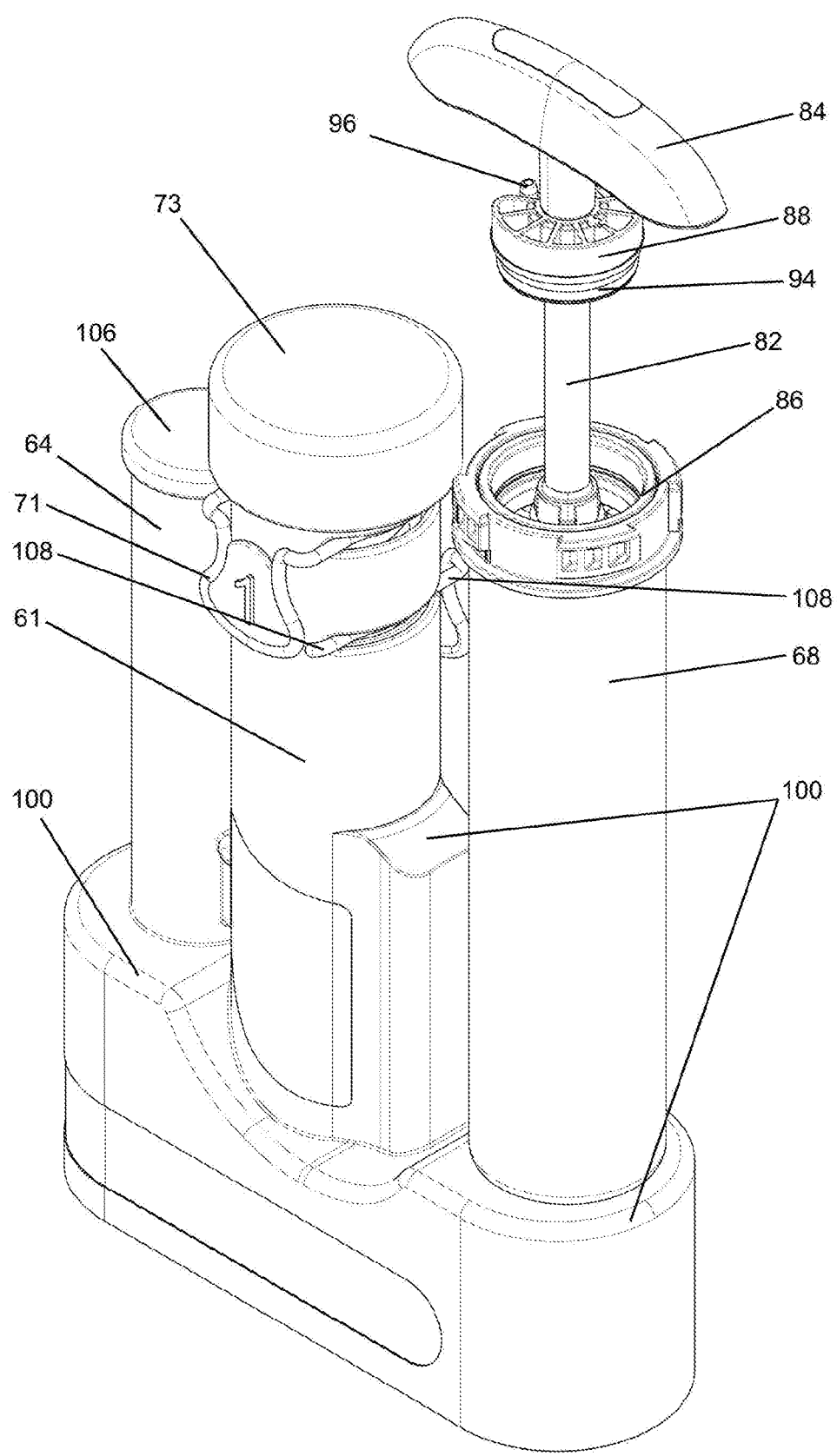
Figure 8:
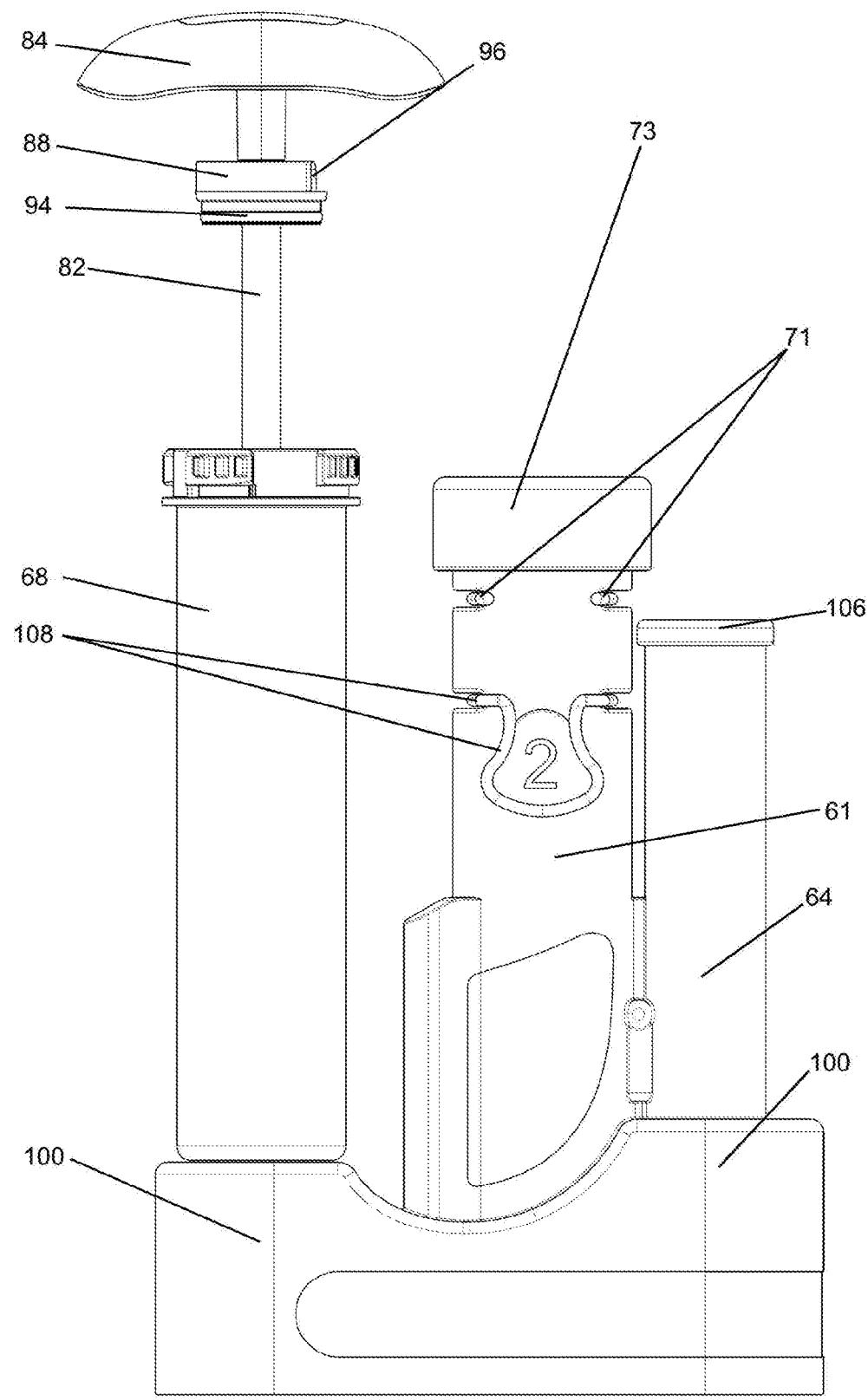
Figure 9:
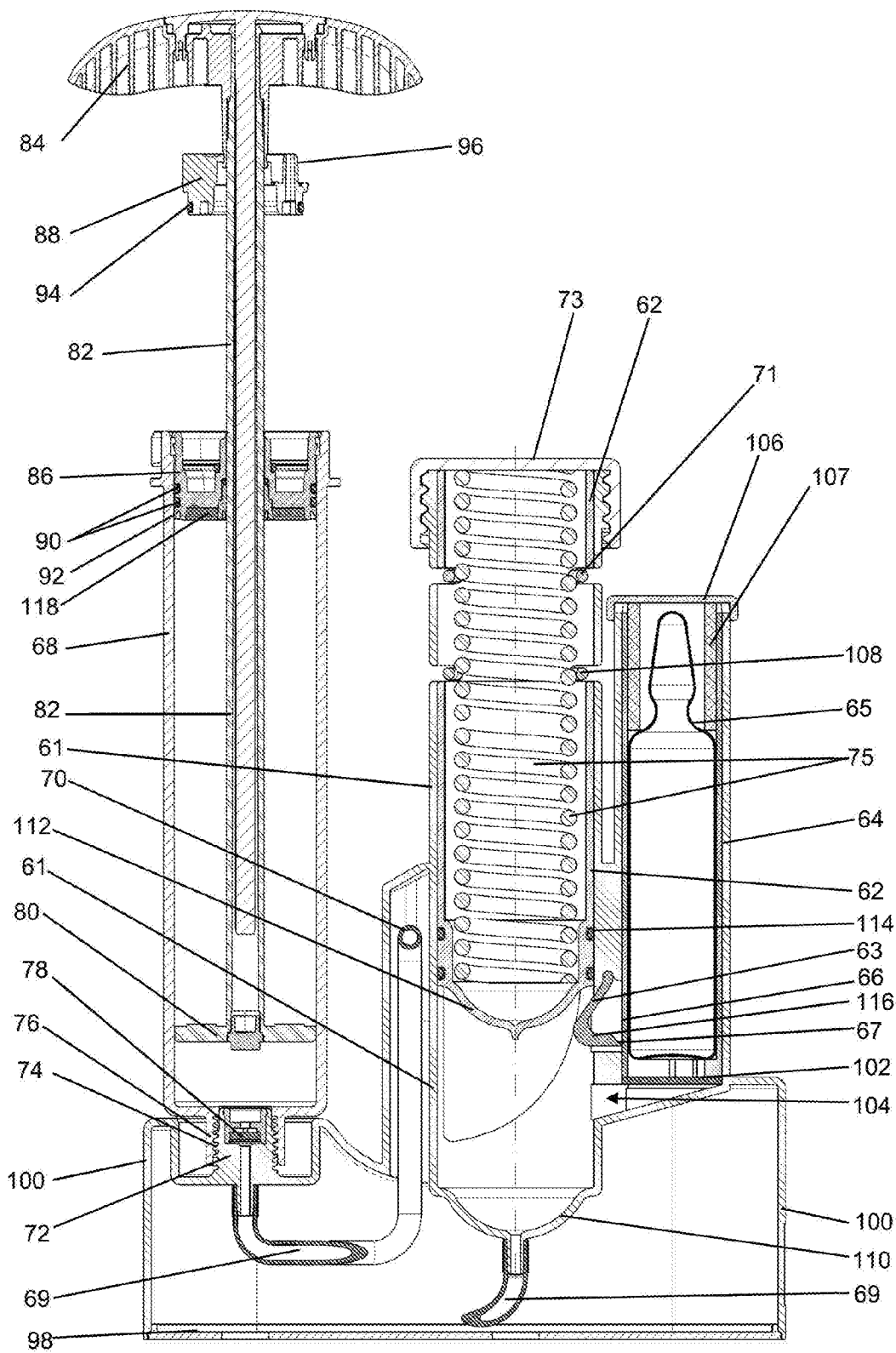
Figure 10:
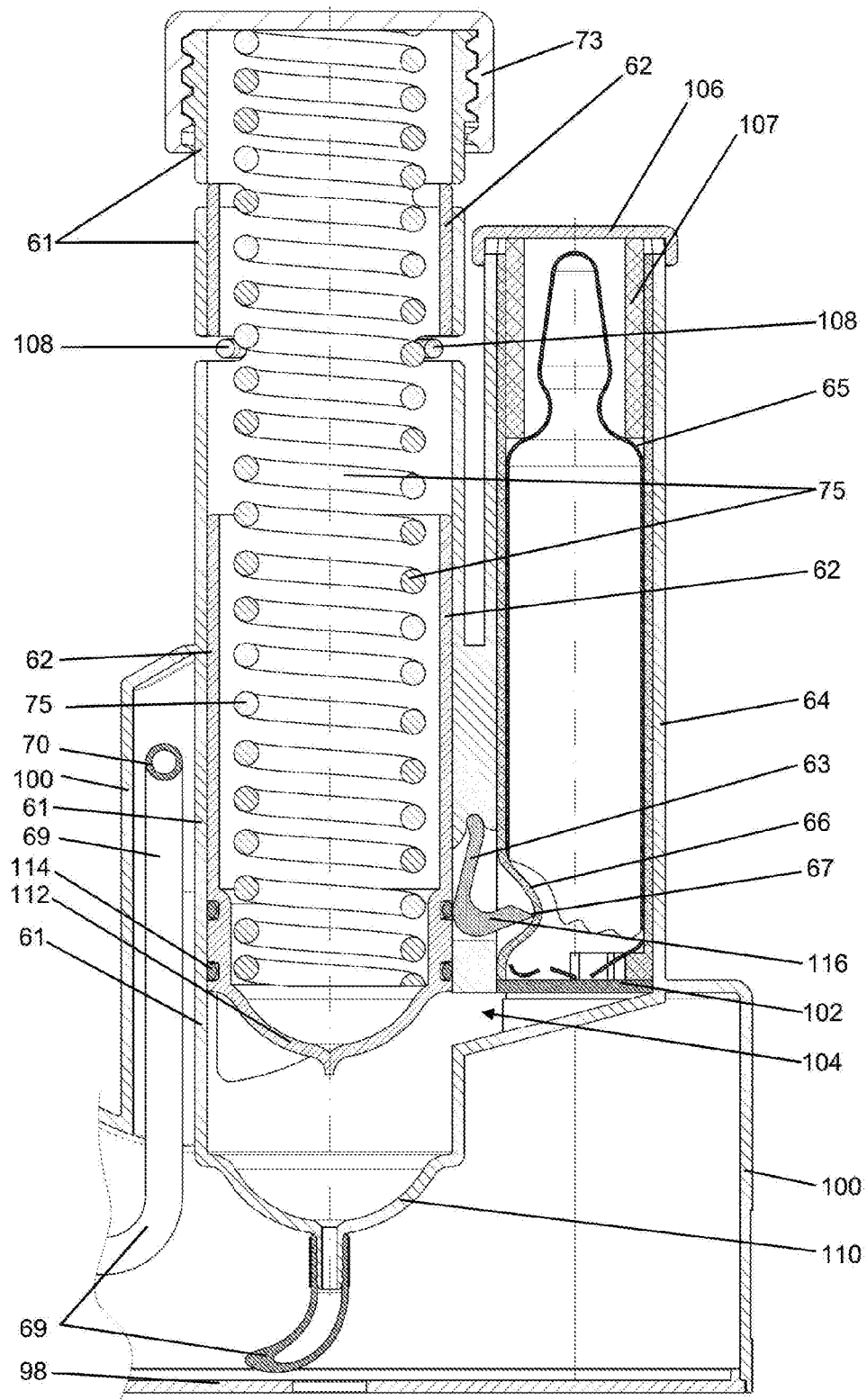
Figure 11:
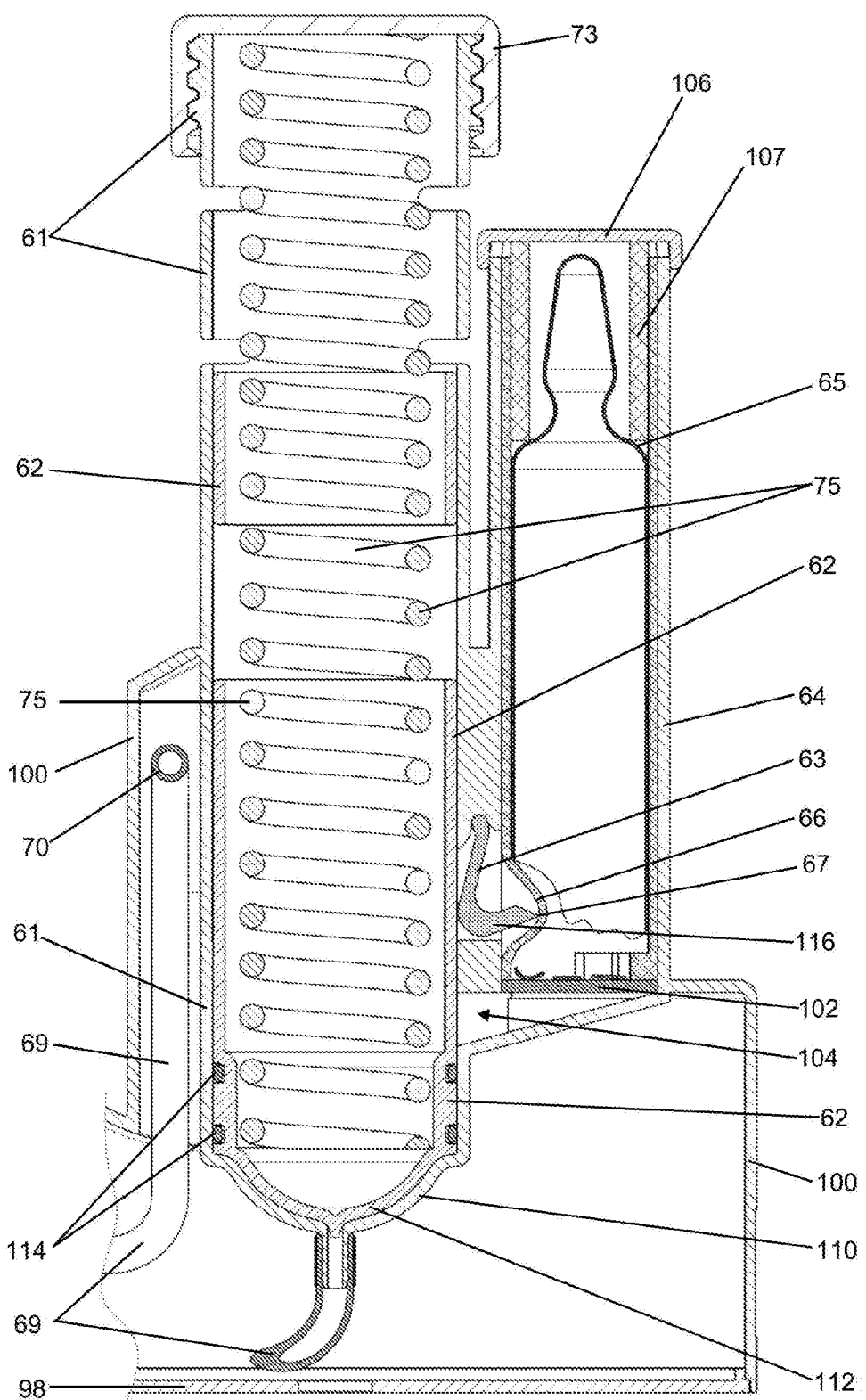
Figure 12:
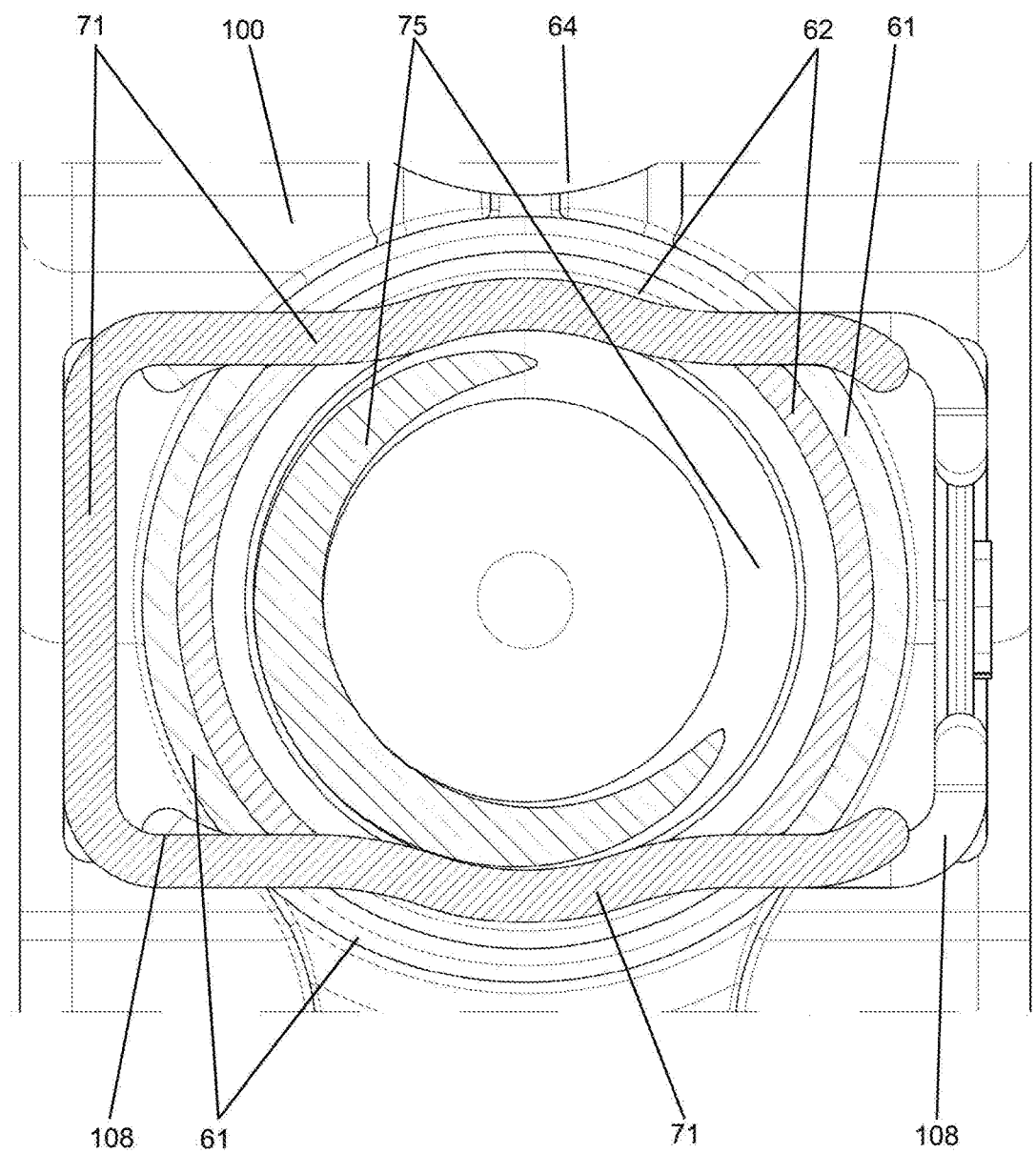

Two further exemplary embodiments of the invention will be explained hereinafter on the basis of twelve figures presented in schematic form, but without thereby restricting the invention. The figures show:

FIG. 1: a schematic perspective part sectional view of a device according to the invention, as a full-prepacked mixing system;

FIG. 2: the device according to FIG. 1 in a schematic side view;

FIG. 3: a schematic cross-sectional view of the device according to the invention according to FIGS. 1 and 2 in an initial situation;

FIG. 4: a schematic cross-sectional view of the device according to the invention according to FIG. 3, wherein the pump plunger is pressed in by a certain amount and the glass ampoule is opened;

FIG. 5: a schematic perspective cross-sectional view of the device according to the invention according to FIG. 4;

FIG. 6: a schematic cross-sectional view of the device according to the invention according to FIGS. 4 and 5, wherein the pump plunger is fully pressed in and the monomer liquid has been pressed into the cartridge;

FIG. 7: a schematic perspective side view of an alternative second device according to the invention;

FIG. 8: the device according to FIG. 7 in a schematic side view, opposite the view according to FIG. 7;

FIG. 9: a schematic cross-sectional view of the second device according to the invention according to FIGS. 7 and 8 in an initial situation;

FIG. 10: a schematic cross-sectional view of a section of the second device according to the invention according to FIG. 9, wherein the pump plunger is pressed in by a certain amount and the glass ampoule is opened;

FIG. 11: a schematic cross-sectional view of the section of the second device according to the invention according to FIG. 10, wherein the pump plunger is fully pressed in and the monomer liquid has been pressed into the cartridge; and FIG. 12: a schematic cross-sectional view of a part section of the second device according to the invention according to FIGS. 7 to 11, wherein the sectional plane runs parallel to the buckle or the latching means.

In the cross-sectional views in FIGS. 3, 4, 6, 9, 10, 11 and 12, sectioned surfaces are identified by shading.

FIGS. 1 to 6 show a first exemplary embodiment of a device according to the invention for mixing polymethyl methacrylate bone cement and for storing the parent components of the bone cement, specifically a monomer liquid and a cement powder, in different views. The device is suitable for implementing a method according to the invention.

The device comprises a hollow cylinder 1 in which a pump plunger 2, which is cylindrical in some regions, is arranged to be axially movable. An opening device 3 in the form of a short lever 3 is mounted at an outer side wall of the hollow cylinder 1 so as to be pivotable about an axis perpendicular to the axial direction of movement of the pump plunger 2. A recess in the form of a window is located in the cylinder casing of the hollow cylinder 1, in the region of the lever 3, through which window the lever 3 extends into the interior of the hollow cylinder 1 in an initial position (see FIGS. 1 to 3). Accordingly, FIGS. 1 to 3 show the initial position of the device, which is defined by the way in which the lever 3 is placed and by the position of the pump plunger 2.

Directly next to the lever 3, a receptacle 4 for a glass ampoule 5 is provided, into which the glass ampoule 5 is already inserted. The glass ampoule 5 is filled with a monomer liquid (not illustrated). At its base (at the bottom in FIGS. 1 to 3), the glass ampoule 5 rests on an edge or a projection. In the region of the window or the recess in the hollow cylinder 1, the receptacle 4 is delimited only by a deformable side wall 6 made of rubber or another flexible synthetic material. The lever 3 abuts against the deformable side wall 6 via an edge 7 or a wedge 7. The glass ampoule 5 is unopened in the initial position (FIGS. 1 to 3). The initial position is therefore suitable for storing the monomer liquid or the parent components.

A cartridge 8 comprising a cylindrical interior is arranged on the other side next to the hollow cylinder 1 with the pump plunger 2. A cement powder (not illustrated) is located in the cartridge 8, as a second parent component of the PMMA bone cement. At the bottom side (at the bottom in FIGS. 1 to 6), the cartridge 8 is connected to the base of the hollow cylinder 1 by way of a connecting line 9. The connecting line 9 forms a loop 10 between the cartridge 8 and the hollow cylinder 1, which loop is arranged above the base of the glass ampoule 5. This prevents the monomer liquid from being able to flow directly into the interior of the cartridge 8 when the glass ampoule 5 is open. The connecting line 9 leads into the cartridge 8 via a fitting 12. The fitting 12 is provided with an outer thread 14, onto which an inner thread 16 at the front side of the cartridge 8 is screwed. The cartridge 8 is therefore releasably connected to the fitting 12. Once the PMMA bone cement has been mixed in the interior of the cartridge 8, a delivery pipe (not shown) can be screwed into the inner thread 16, through which delivery pipe the ready-mixed PMMA bone cement can be driven out of the cartridge 8 and applied.

A filter 18 which is impermeable to powder and permeable to liquid is located in the fitting 12, in the connecting line 9, at the point of connection to the cartridge 8. This filter 18 prevents the cement powder from falling out of the interior of the cartridge 8 into the connecting line 9 and reacting there with the monomer liquid, thus avoiding that PMMA blocks the connecting line 9 as it cures. The mouth of the connecting line 9 leading into the interior of the cartridge 8 is formed as a nozzle. The nozzle is preferably formed according to U.S. Pat. No. 8,662,736 B4.

In the interior of the cartridge 8, a mixing device 20 comprising several mixing blades 20 is provided, which, by means of a mixing rod 22, is or are axially movable in the interior of the cartridge 8 and is or are rotatable in the interior of the cartridge 8. For this purpose, the mixing rod 22 is guided into the interior of the cartridge 8 through a gas-tight duct. The mixing rod 22 terminates in a handle 24 outside the cartridge 8, by means of which the mixing rod 22, and therefore the mixing blades 20, are manually movable. The mixing blades 20 can be used to mix the cement powder with the monomer liquid after the monomer liquid has been introduced into the interior of the cartridge 8 through the connecting line 9.

The rear end of the cartridge 8 (at the top in FIGS. 1 to 6) is closable by means of a two-piece delivery plunger 26, 28. The delivery plunger 26, 28 consists of a sterilization plunger 26 and a sealing plunger 28. The sterilization plunger 26 is already inserted into the interior of the cartridge 8 in FIGS. 1 to 3, while the sealing plunger 28 is still separate from the sterilization plunger 26 in FIGS. 1 to 3. When the sealing plunger 28 is not yet inserted into the sterilization plunger 26, the cartridge 8, including the interior and the cement powder in the interior, can be sterilized with the aid of a sterilizing gas such as ethylene oxide. For this purpose, the sterilization plunger 26 has a filter 58 which is permeable to gas and impermeable to powder, which enables gas to enter but prevents cement powder from exiting the interior of the cartridge 8. Next, the sealing plunger 28 can be inserted into the sterilization plunger 26, and both together form the delivery plunger 26, 28, which can later be used to drive out the PMMA bone cement ready-mixed in the interior of the cartridge 8 through the front opening or a delivery pipe (not shown) screwed into said front opening, in that the delivery plunger 26, 28 is driven forward in the direction of the opening.

The sterilization plunger 26 has two circumferential seals 30, by means of which the sterilization plunger 26 is sealed against the inner wall of the cartridge 8. In addition, a wiper lip 32 is located at the front side of the sterilization plunger 26, which wiper lip can be used to wipe the mixed PMMA bone cement off the inner walls of the cartridge 8 and drive it forward in the cartridge 8. The sealing plunger 28 also has a circumferential seal 34, by means of which it is sealed against the sterilization plunger 26. An additional seal is provided at the sterilization plunger 26, for further sealing the connection between the sealing plunger 28 and the sterilization plunger 26. A vacuum port 36 is located in the sealing plunger 28, which vacuum port is connected to a feed-through through the sealing plunger 28. As a result, the interior of the cartridge 8 can be evacuated even when the sealing plunger 28 is inserted into the sterilization plunger 26. The PMMA bone cement or the cement paste in the interior of the cartridge 8 can therefore be mixed under vacuum or under reduced pressure in order to reduce the number of possible air inclusions.

At the bottom side, the device is delimited by a stand 38 with a flat rest, on which stand the device can be placed on a flat surface. In addition, the inner parts of the device are enclosed by a housing 40 made of plastic. The hollow cylinder 1 is made in one piece with the housing 40. Only the cartridge 8 can be separated from the stand 38 and the housing 40. The housing 40 and the stand 38 can also be regarded jointly as a stand 38, 40 since together they form a continuous part which forms the lower part of the device that holds the device after it has been put in place.

A filter 42 and/or a screen 42 is/are arranged in the receptacle 4, below the glass ampoule 5, which filter and/or screen hold(s) back splinters and fragments of the glass ampoule 5 when it is broken open. An inclined plane is located below the filter 42 and/or the screen 42, along which the monomer liquid flows out of the opened glass ampoule 5 through a mouth 44 into the hollow cylinder 1, i.e. flows into the hollow cylinder 1 by way of a fluid connection 44 between the hollow cylinder 1 and the receptacle 4. The upper side of the receptacle 4 is closed by a lid 46. A pipe 47 made of a flexible synthetic material, for example a foam or rubber, is located in the lid 46, which pipe is used to press the glass ampoule 5 onto the edge at the base of the receptacle 4, thereby positioning it in the receptacle 4.

A securing pin 48 is located in the pump plunger 2, as a latching device 48. The securing pin 48 is provided with a handle by means of which the securing pin 48 can be drawn out of the pump plunger 2 manually. The securing pin 48 is placed so as to pass through the pump plunger 2 and prevents the pump plunger 2 from being able to be pressed into the hollow cylinder 1 deeper than to the beginning of the hollow cylinder 1. When the pump plunger 2 has been pressed into the hollow cylinder 1 until the securing pin 48 or the latching device 48 blocks its movement, the lever 3 is pivoted about its axis due to the movement of the pump plunger 2 and pressed against the deformable side wall 6 by the pump plunger 2. For this purpose, the lever 3 is wide enough, or has a web 56 perpendicular to the pivot axis which is long enough, so that the deformation of the deformable side wall 6 is sufficient to break open the glass ampoule 5 in the receptacle 4. The deformable side wall 6 deforms, and the glass ampoule 5 in the interior of the receptacle 4 is broken open. However, the securing pin 48 still prevents the pump plunger 2 from being pressed further into the hollow cylinder 1. This situation is illustrated in FIGS. 4 and 5.

The hollow cylinder 1 is shaped in the manner of a funnel at its bottom surface 50 or at its base 50, the mouth leading into the connecting line 9 being located at the lowest point of said funnel. As a result, the base 50 of the hollow cylinder 1 routes monomer liquid contained therein into the connecting line 9. The pump plunger 2, on its underside 52, is shaped so as to match the base 50 of the hollow cylinder 1. As a result, the lower face 52 of the pump plunger 2 can be used to press virtually all of the monomer liquid located in the hollow cylinder 1 into the connecting line 9. In addition, the highest point in the hollow cylinder 1 is formed by the mouth 44 in the situation shown in FIGS. 4 and 5, so that air can escape out of the hollow cylinder 1 through the mouth 44. The monomer liquid from the broken glass ampoule 5 therefore flows into the hollow cylinder 1 through the filter 42 and/or the screen 42 and through the mouth 44. However, the monomer liquid will not pass the vertex formed by the loop 10 if it is not pressed beyond that point with the aid of the pump plunger 2. This serves to prevent a premature reaction of the monomer liquid with the PMMA bone cement powder in the interior of the cartridge 8.

The securing pin 48 can now be drawn out of the pump plunger 2. Then, the pump plunger 2 can be pressed deeper into the hollow cylinder 1 in order to press the monomer liquid through the connecting line 9 into the interior of the cartridge 8. The time required to draw out the securing pin 48 is enough to permit the monomer liquid to flow from the receptacle 4 into the hollow cylinder 1. The pump plunger 2 is sealed against the inner wall of the hollow cylinder 1 by means of two circumferential seals 54 to prevent the monomer liquid from making its way to the outside between the pump plunger 2 and the hollow cylinder 1. By completely inserting the pump plunger 2 into the hollow cylinder 1, the monomer liquid is pressed out of the hollow cylinder 1 into the interior of the cartridge 8, where it can be mixed with the bone cement with the aid of the mixing device 20. This situation is shown in FIG. 6. The securing pin 48 has been drawn out of the pump plunger 2, and there remains only a hole 59 in which the securing pin 48 had been before. While mixing, a vacuum or a reduced pressure can be produced in the interior of the cartridge 8 by way of the vacuum port 36.

The PMMA bone cement mixed in the interior of the cartridge 8 can be used by screwing the cartridge 8 off the remaining device, screwing a delivery pipe into the inner thread 16, and inserting the cartridge 8 into a delivery device in the form of a dispenser gun, by means of which the delivery plunger 26, 28 is driven forward in the direction of the front opening, thereby pressing the ready-mixed bone cement out of the interior of the cartridge 8. The pump plunger 2 is actuated manually in the first embodiment according to FIGS. 1 to 6, i.e. pressed into the hollow cylinder 1 by hand.

FIGS. 7 to 12 show illustrations of a second alternative exemplary embodiment of a device according to the invention for mixing polymethyl methacrylate bone cement and for storing the parent components of the bone cement, specifically a monomer liquid and a cement powder, in which a pump plunger 62 is not manually actuated and pressed into a hollow cylinder 61 but by means of an internal energy store 75. This device is also suitable for implementing a method according to the invention.

The second alternative device comprises a hollow cylinder 61 in which a pump plunger 62, which is cylindrical in some regions, is arranged to be axially movable. The two part sections of the pump plunger 62 which can be seen in the cross-sectional views of FIGS. 9, 10 and 11 are securely connected to each other. The pump plunger 62 is therefore made in one piece, as can also be seen in FIG. 12. An opening device 63 in the form of a lever 63 is mounted at an outer side wall of the hollow cylinder 61 so as to be pivotable about an axis perpendicular to the axial direction of movement of the pump plunger 62. A recess in the form of a window is located in the cylinder casing of the hollow cylinder 61, in the region of the lever 63, through which window the lever 63 extends into the interior of the hollow cylinder 61 in an initial position (see FIG. 9). FIGS. 7 to 9 and 12 show the initial position of the second alternative device, which is defined by the way in which the lever 63 is placed and by the position of the pump plunger 62.

Directly next to the lever 63, a receptacle 64 for a glass ampoule 65 is provided, into which the glass ampoule 65 is already inserted. The glass ampoule 65 is filled with a monomer liquid (not illustrated). At its base (at the bottom in FIGS. 7 to 9), the glass ampoule 65 rests on an edge or a projection. In the region of the window or the recess in the hollow cylinder 61, the receptacle 64 is delimited only by a deformable side wall 66 made of rubber or another flexible synthetic material. The lever 63 abuts against the deformable side wall 66 via an edge 67 or a wedge 67. The glass ampoule 65 is unopened in the initial position (FIGS. 7 to 9 and 12). The initial position is therefore suitable for storing the monomer liquid or the parent components.

A cartridge 68 comprising a cylindrical interior is arranged on the other side next to the hollow cylinder 61 with the pump plunger 62. A cement powder (not illustrated) is located in the cartridge 68, as a second parent component of the PMMA bone cement. At the bottom side (at the bottom in FIGS. 7 to 12), the cartridge 68 is connected to the base of the hollow cylinder 61 by way of a connecting line 69. The connecting line 69 forms a loop 70 between the cartridge 68 and the hollow cylinder 61, which loop is arranged above the base of the glass ampoule 65. This prevents the monomer liquid from being able to flow directly into the interior of the cartridge 68 when the glass ampoule 65 is open. The pump plunger 62 cannot be pressed into the hollow cylinder 61 in the initial position (FIGS. 7 to 9 and 12) as the pump plunger 62 is connected to the hollow cylinder 61 with the aid of a buckle 71 as a latching means 71. The pump plunger 62 cannot be pressed into the hollow cylinder 61 until the buckle 71 is removed.

The connecting line 69 leads into the cartridge 68 via a fitting 72. The upper side of the hollow cylinder 61 is closed by a screwed-on cap 73, which supports a tensioned pressure spring 75 for actuating the pump plunger 62. For this purpose, the tensioned pressure spring 75 is supported by the cap 73 and the pump plunger 62 and is under compressive stress, at least in the initial position shown in FIGS. 7 to 9 and 12 and also in the intermediate position shown in FIG. 10, so that the pump plunger 62 can be moved in the hollow cylinder 61 by means of the pressure spring 75 until it comes to a stop. Preferably, the pressure spring 75 continues to be tensioned at this point. The precise arrangement of the first buckle 71 is shown in FIG. 12 as a schematic cross-sectional view of a part section of the second device according to the invention, wherein the sectional plane runs parallel to the first buckle 71 or the latching means 71. The pressure spring 75 preferably consists of a spring steel.

The fitting 72 is provided with an outer thread 74, onto which an inner thread 76 at the front side of the cartridge 68 is screwed. The cartridge 68 is therefore releasably connected to the fitting 72. Once the PMMA bone cement has been mixed in the interior of the cartridge 68, a delivery pipe (not shown) can be screwed into the inner thread 76, through which delivery pipe the ready-mixed PMMA bone cement can be driven out of the cartridge 68 and applied.

A filter 78 which is impermeable to powder and permeable to liquid is located in the fitting 72, in the connecting line 69, at the point of connection to the cartridge 68. This filter 78 prevents the cement powder from falling out of the interior of the cartridge 68 into the connecting line 69 and reacting there with the monomer liquid, thus avoiding that PMMA blocks the connecting line 69 as it cures. The mouth of the connecting line 69 leading into the interior of the cartridge 68 is formed as a nozzle. The nozzle is preferably formed according to U.S. Pat. No. 8,662,736 B4.

In the interior of the cartridge 68, a mixing device 80 comprising several mixing blades 80 is provided, which, by means of a mixing rod 82, is or are axially movable in the interior of the cartridge 68 and is or are rotatable in the interior of the cartridge 68. For this purpose, the mixing rod 82 is guided into the interior of the cartridge 68 through a gas-tight duct. The mixing rod 82 terminates in a handle 84 outside the cartridge 68, by means of which the mixing rod 82, and therefore the mixing blades 80, are manually movable. The mixing blades 80 can be used to mix the cement powder with the monomer liquid after the monomer liquid has been introduced into the interior of the cartridge 68 through the connecting line 69.

The rear end of the cartridge 68 (at the top in FIGS. 7 to 12) is closable by means of a two-piece delivery plunger 86, 88. The delivery plunger 86, 88 consists of a sterilization plunger 86 and a sealing plunger 88. The sterilization plunger 86 is already inserted into the interior of the cartridge 68 in FIGS. 7 to 9, while the sealing plunger 88 is still separate from the sterilization plunger 86 in FIGS. 7 to 9. When the sealing plunger 88 is not yet inserted into the sterilization plunger 86, the cartridge 68, including the interior and the cement powder in the interior, can be sterilized with the aid of a sterilizing gas such as ethylene oxide. For this purpose, the sterilization plunger 86 has a filter 118 which is permeable to gas and impermeable to powder, which enables gas to enter but prevents cement powder from exiting the interior of the cartridge 68. Next, the sealing plunger 88 can be inserted into the sterilization plunger 86, and both together form the delivery plunger 86, 88, which can later be used to drive out the PMMA bone cement ready-mixed in the interior of the cartridge 68 through the front opening or a delivery pipe (not shown) screwed into said front opening, in that the delivery plunger 86, 88 is driven forward in the direction of the opening.

The sterilization plunger 86 has two circumferential seals 90, by means of which the sterilization plunger 86 is sealed against the inner wall of the cartridge 68. In addition, a wiper lip 92 is located at the front side of the sterilization plunger 86, which wiper lip can be used to wipe the mixed PMMA bone cement off the inner walls of the cartridge 68 and drive it forward in the cartridge 68. The sealing plunger 88 also has a circumferential seal 94, by means of which it is sealed against the sterilization plunger 86. An additional seal is provided at the sterilization plunger 86, for further sealing the connection between the sealing plunger 88 and the sterilization plunger 86. A vacuum port 96 is located in the sealing plunger 88, which vacuum port is connected to a feed-through through the sealing plunger 88. As a result, the interior of the cartridge 68 can be evacuated even when the sealing plunger 88 is inserted into the sterilization plunger 86. The PMMA bone cement or the cement paste in the interior of the cartridge 68 can therefore be mixed under vacuum or under reduced pressure in order to reduce the number of possible air inclusions.

At the bottom side, the device is delimited by a stand 98 with a flat rest, on which stand the device can be placed on a flat surface. In addition, the inner parts of the device are enclosed by a housing 100 made of plastic. The hollow cylinder 61 is made in one piece with the housing 100. Only the cartridge 68 can be separated from the stand 98 and the housing 100. The housing 100 and the stand 98 can also be regarded jointly as a stand 98, 100 since together they form a continuous part which forms the lower part of the device that holds the device after it has been put in place.

A filter 102 and/or a screen 102 is/are arranged in the receptacle 64, below the glass ampoule 65, which filter and/or screen hold(s) back splinters and fragments of the glass ampoule 65 when it is broken open. An inclined plane is located below the filter 102 and/or the screen 102, along which the monomer liquid flows out of the opened glass ampoule 65 through a mouth 104 into the hollow cylinder 61, i.e. flows into the hollow cylinder 61 by way of a fluid connection 104 between the hollow cylinder 61 and the receptacle 64. The upper side of the receptacle 64 is closed by a lid 106. A pipe 107 made of a flexible synthetic material, for example a foam or rubber, is located in the lid 106, which pipe is used to press the glass ampoule 65 onto the edge at the base of the receptacle 64, thereby positioning it in the receptacle 64.

A second buckle 108 is provided as a latching device 108 in matching recesses in the hollow cylinder 61 and the pump plunger 62. The second buckle 108 prevents the pump plunger 62 from being able to be pressed into the hollow cylinder 61 deeper than to the mouth 104. Therefore, after the first buckle 71 has been removed, the pressure spring 75 presses the pump plunger 62 into the hollow cylinder 61 until the pump plunger 62 is held or retained by the second buckle 108 in the intermediate position. This position is shown in FIG. 10.

Both buckles 71, 108 are provided with handles by means of which they can be drawn out of the recesses manually. In addition, the numbers "1" and "2" are indicated as markings on the handles of the buckles 71, 108 to instruct the user in which order the two buckles 71, 108 are to be drawn out. When the pump plunger 62 has been pressed into the hollow cylinder 61 by the pressure spring 75 until the second buckle 108 or the latching device 108 blocks its movement, the lever 63 is pivoted about its axis due to the movement of the pump plunger 62 and pressed against the deformable side wall 66 by the pump plunger 62. For this purpose, the lever 63 is wide enough, or has a web 116 perpendicular to the pivot axis which is long enough, so that the deformation of the deformable side wall 66 is sufficient to break open the glass ampoule 65 in the receptacle 64. The deformable side wall 66 deforms, and the glass ampoule 65 in the interior of the receptacle 64 is broken open. However, the second buckle 108 still prevents the pump plunger 62 from being pressed further into the hollow cylinder 61. This situation is illustrated in FIG. 10.

The hollow cylinder 61 is shaped in the manner of a funnel at its bottom surface 110 or at its base 110, the mouth leading into the connecting line 69 being located at the lowest point of said funnel. As a result, the base 110 of the hollow cylinder 61 routes monomer liquid contained therein into the connecting line 69. The pump plunger 62, on its underside 112, is shaped so as to match the base 110 of the hollow cylinder 61. As a result, the lower face 112 of the pump plunger 62 can be used to press virtually all of the monomer liquid located in the hollow cylinder 61 into the connecting line 69. In addition, the highest point in the hollow cylinder 61 is formed by the mouth 104 in the situation shown in FIG. 10, so that air can escape out of the hollow cylinder 61 through the mouth 104. The monomer liquid from the broken glass ampoule 65 therefore flows into the hollow cylinder 61 through the filter 102 and/or the screen 102 and through the mouth 104. However, the monomer liquid will not pass the vertex formed by the loop 70 if it is not pressed beyond that point with the aid of the pump plunger 62. This serves to prevent a premature reaction of the monomer liquid with the PMMA bone cement powder in the interior of the cartridge 68.

The second buckle 108 can now be drawn out of the pump plunger 62. Then, the pump plunger 62 is pressed deeper into the hollow cylinder 61 by the pressure spring 75, thereby pressing the monomer liquid through the connecting line 69 into the interior of the cartridge 68. The time required to draw out the second buckle 108 is enough to permit the monomer liquid to flow from the receptacle 64 into the hollow cylinder 61. The pump plunger 62 is sealed against the inner wall of the hollow cylinder 61 by means of two circumferential seals 114 to prevent the monomer liquid from making its way to the outside between the pump plunger 62 and the hollow cylinder 61. By completely inserting the pump plunger 62 into the hollow cylinder 61, the monomer liquid is pressed out of the hollow cylinder 61 into the interior of the cartridge 68, where it can be mixed with the bone cement with the aid of the mixing device 80. This situation is illustrated in FIG. 11. The second buckle 108 has been drawn out. While mixing, a vacuum or a reduced pressure can be produced in the interior of the cartridge 68 by way of the vacuum port 96.

The PMMA bone cement mixed in the interior of the cartridge 68 can be used by screwing the cartridge 68 off the remaining device, screwing a delivery pipe into the inner thread 76, and inserting the cartridge 68 into a delivery device in the form of a dispenser gun, by means of which the delivery plunger 86, 88 is driven forward in the direction of the front opening, thereby pressing the ready-mixed bone cement out of the interior of the cartridge 68. By contrast with the first embodiment, the pump plunger 62 is therefore not actuated manually in the second embodiment according to FIGS. 7 to 12 but by means of a tensioned pressure spring 75, i.e. pressed into the hollow cylinder 61 by means of the pressure spring 75.

The features of the invention disclosed in the above description, the claims, figures and exemplary embodiments can be relevant both individually and in combination for implementing the various embodiments of the invention.

LIST OF REFERENCE NUMERALS 1, 61 Hollow cylinder
2, 62 Pump plunger
3, 63 Opening device/lever
4, 64 Receptacle
5, 65 Glass ampoule
6, 66 Deformable side wall
7, 67 Wedge/edge
8, 68 Cartridge
9, 69 Connecting line
10, 70 Loop
12, 72 Fitting
14, 74 Outer thread
16, 76 Inner thread 18, 78 Filter which is impermeable to powder and permeable to liquid
20, 80 Mixing blade
22, 82 Mixing rod
24, 84 Handle
26, 86 Sterilization plunger
28, 88 Sealing plunger
30, 90 Seal
32, 92 Wiper lip
34, 94 Seal
36, 96 Vacuum port
38, 98 Stand
40, 100 Housing
42, 102 Screen/filter
44, 104 Mouth leading into the hollow cylinder/fluid connection
46, 106 Lid
47, 107 Pipe
48 Securing pin with handle/latching device
50, 110 Base of the hollow cylinder
52, 112 Lower face of the pump plunger
54, 114 Seal
56, 116 Web/transverse piece of the lever
58, 118 Filter which is permeable to gas and impermeable to powder
58 Duct
71 Buckle/latching means
73 Screw cap
75 Pressure spring
108 Buckle/latching device

We claim:

1. A device for mixing bone cement and for storing the parent components of the bone cement, wherein at least a monomer liquid and a cement powder are parent components of the bone cement, the device comprising:
   a cartridge comprising an interior for mixing the bone cement, wherein the interior is closed on one side by a movable delivery plunger;
   a receptacle comprising side walls for receiving a monomer liquid container, which side walls are closed at least in some regions, wherein the receptacle has at least one deformable closed side wall;
   at least one selected from a screen and a filter which is or are arranged below the receptacle so that the contents of the opened monomer liquid container flow through the at least one selected from the screen and the filter;
   a connecting line through which the monomer liquid is to be routed into the interior of the cartridge;
   a hollow cylinder connected to the connecting line and which is connected to the receptacle by way of a fluid connection so that the hollow cylinder is arranged in a fluid line between the receptacle and the interior of the cartridge, wherein a pump plunger is arranged in the hollow cylinder, which is axially displaceable in the hollow cylinder; and
   an opening device movably mounted against the deformable side wall of the receptacle, wherein the opening device extends into the hollow cylinder, wherein, by pressing the pump plunger into the hollow cylinder, the opening device is to be pressed against the deformable side wall of the receptacle so that the deformable side wall deforms in such a way that a monomer liquid container located in the receptacle is to be opened by the pressure of the opening device.

2. The device according to claim 1, wherein the monomer liquid is flowable out of the opened monomer liquid container into the hollow cylinder, and the connecting line connects the hollow cylinder to the interior of the cartridge in such a way that, by means of the pump plunger, the monomer liquid is to be pressed out of the hollow cylinder through the connecting line into the interior of the cartridge by pressing the pump plunger into the hollow cylinder.

3. The device according to claim 1, further comprising:
   a mixing device, which is externally operable, is arranged in the cartridge, wherein the mixing device is operable by way of a mixing rod which is guided through a feed-through in the delivery plunger into the interior of the cartridge and which is movably mounted.

4. The device according to claim 1, wherein the cement powder is contained in the interior of the cartridge.

5. The device according to claim 1, wherein a powder filter that is impermeable to the cement powder and permeable to the monomer liquid is arranged between the connecting line and the interior of the cartridge.

6. The device according to claim 5, wherein at least one selected from:
   the device has a stand in which at least part of the connecting line is arranged, wherein the cartridge is releasably connected to the stand by way of a screw thread; and
   the powder filter that is impermeable to the cement powder and permeable to the monomer liquid is optionally arranged in the connection between the cartridge and the stand.

7. The device according to claim 1, wherein the receptacle leads into the hollow cylinder at a circumferential surface of the hollow cylinder.

8. The device according to claim 1, wherein the connecting line is connected to the hollow cylinder at the lowest point of the hollow cylinder, wherein the pump plunger is arranged on the opposite side of the hollow cylinder.

9. The device according to claim 1, wherein the hollow cylinder has, on the side opposite the pump plunger, a conical, semi-conical or otherwise downwardly tapering base, wherein the face of the pump plunger, which faces the base of the hollow cylinder, forms a negative shape of the base form-fitting the shape of the base.

10. The device according to claim 1, wherein the device has a tensioned pressure spring and at least one detent, wherein the pressure spring and/or the pump plunger is or are releasably arrested by the detent, wherein the pressure spring exerts a pressure on the pump plunger, when the detent is released so that the pump plunger is pressed into the hollow cylinder.

11. The device according to claim 1, wherein the connecting line between the hollow cylinder and the interior of the cartridge has an upwardly pointing loop, wherein the highest point of the loop is located above a mouth of the receptacle leading into the hollow cylinder.

12. The device according to claim 1, wherein the volume in the hollow cylinder is smaller than or equal to the volume of the monomer liquid in the monomer liquid container.

13. The device according to claim 1, wherein the opening device is a lever which is mounted against the receptacle to be rotatable about an axis, wherein a free end of the lever is pressable against the deformable side wall of the receptacle by the pump plunger, so that the free end of the lever deforms the deformable side wall in such a way that the monomer liquid container located in the receptacle and matching the receptacle is to be opened by the pressure of the free end of the lever, is to be broken open or split open or punctured.

14. The device according to claim 13, wherein the free end, with the lever, is arranged inside the hollow cylinder, and abuts against the deformable side wall, in such a way that the lever, starting from the axis with the free end and the deformable side wall, forms a triangle with a web as a leg opposite the corner formed by the axis of rotation, wherein the triangle is arranged in the hollow cylinder.

15. The device according to claim 1, wherein the receptacle is a hollow cylinder and/or the receptacle consists of an elastomer or comprises an insert made of an elastomer, wherein the elastomer has a Shore hardness of greater than 60.

16. The device according to claim 1, wherein a shoulder for supporting the monomer liquid container is arranged in the receptacle, wherein the shoulder is smaller than half the area of the base of the monomer liquid container or the cross-section of the monomer liquid container.

17. The device according to claim 1, wherein, upon a movement of the pump plunger into the hollow cylinder, a free end of the opening device presses on the deformable side wall in such a way that the vector of the force has a component which is directed towards the screen and/or filter and/or which presses a monomer liquid container inserted in the receptacle into the receptacle in the direction of a shoulder.

18. The device according to claim 1, wherein the opening device extends into the hollow cylinder above the fluid connection.

19. The device according to claim 1, wherein the pump plunger is fixable in place by a manually releasable latching device which, after an axial displacement of the pump plunger over the opening device in the hollow cylinder, locks the pump plunger above a mouth of the fluid connection to the receptacle in the hollow cylinder, so that the pump plunger in the hollow cylinder is not movable over the mouth of the fluid connection when the latching device is not released, wherein the latching device is arranged on or in the pump plunger or extends through the pump plunger.

20. A method for mixing a bone cement chronological comprising:
A) pressing the pump plunger into a hollow cylinder of the device according to claim 1, wherein the opening device is pressed against the deformable side wall of the receptacle as a result of the movement of the pump plunger;
B) opening the monomer liquid container containing the monomer liquid as a result of the deformation of the side wall of the receptacle by the opening device;
C) flowing the monomer liquid out of the opened monomer liquid container and into the hollow cylinder;
D) pressing the pump plunger further into the hollow cylinder and the monomer liquid is thereby pressed out of the hollow cylinder and through a connecting line into the interior of a cartridge, wherein the cement powder is located in the interior of the cartridge; and
E) the monomer liquid and the cement powder are mixed in the interior of the cartridge.

21. The method according to claim 20, wherein the movement of the pump plunger is stopped by a latching device in A) and the latching device is released prior to D) to enable the pump plunger to be pressed further into the hollow cylinder.

22. The method according to claim 20, wherein the pump plunger is pressed into the hollow cylinder by a tensioned spring element, wherein a latching means or a detent, engaging in the pump plunger and/or in the spring element, is released beforehand.

23. The method according to claim 20, wherein the monomer liquid and the cement powder are mixed in the interior by a mixing device in that the mixing device is operated by moving a mixing rod, which is guided into the interior of the cartridge to be rotatable and longitudinally displaceable, wherein, after the mixing process, the mixing rod is withdrawn from the interior of the cartridge until it comes to a stop and, after being withdrawn until it comes to a stop, the mixing rod is breakable at a predetermined breaking point.

24. The method according to claim 20, wherein the cartridge containing the fully mixed cement paste is released from the connecting line, the hollow cylinder and the receptacle, and the fully mixed cement paste is delivered from the interior of the cartridge by the propulsion of a delivery plunger, which is mounted to be axially movable in the cartridge and which delimits the interior of the cartridge on one side.

25. The method according to claim 20, wherein the monomer liquid is movable into the cartridge by a vacuum in the interior of the cartridge, wherein the vacuum in the cartridge is effected by evacuating the interior of the cartridge by means of the delivery plunger arrested against the cartridge.

* * * * *